(12) United States Patent
Akiyama

(10) Patent No.: US 12,343,039 B2
(45) Date of Patent: Jul. 1, 2025

(54) INSERTION DEVICE AND NEEDLE MEMBER

(71) Applicant: TERUMO KABUSHIKI KAISHA, Tokyo (JP)

(72) Inventor: Takeshi Akiyama, Chuo (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 910 days.

(21) Appl. No.: 17/513,796

(22) Filed: Oct. 28, 2021

(65) Prior Publication Data

US 2022/0047304 A1 Feb. 17, 2022

Related U.S. Application Data

(63) Continuation of application No. PCT/JP2020/025091, filed on Jun. 25, 2020.

(30) Foreign Application Priority Data

Aug. 2, 2019 (JP) .................................. 2019-142877

(51) Int. Cl.
*A61B 17/34* (2006.01)
*A61B 5/1486* (2006.01)

(52) U.S. Cl.
CPC ...... *A61B 17/3468* (2013.01); *A61B 5/14865* (2013.01); *A61B 2560/063* (2013.01)

(58) Field of Classification Search
None
See application file for complete search history.

(56) References Cited

U.S. PATENT DOCUMENTS 5,568,806 A * 10/1996 Cheney, II ........... A61B 5/6849
600/373
2005/0077688 A1* 4/2005 Voegele ............. A61B 17/3462
277/628
(Continued)

FOREIGN PATENT DOCUMENTS

CN 107205702 A 9/2017
JP 2010-179100 A 8/2010
(Continued)

OTHER PUBLICATIONS

Extended European Search Report issued in connection with EP Appl. Ser. No. 20849815.4 dated Jul. 13, 2022 (9 pages).
(Continued)

*Primary Examiner* — Jacqueline Cheng
*Assistant Examiner* — Samuel C Kim
(74) *Attorney, Agent, or Firm* — Foley & Lardner LLP

(57) ABSTRACT

An insertion device for inserting a medical device into a living body includes: a needle portion internally defining an accommodation space configured to accommodate the medical device and configured to be inserted into a living body together with the medical device accommodated in the accommodation space; and a movable portion that is movable with respect to the needle portion in the accommodation space in a direction of insertion of the needle portion. The needle portion comprises a clamping portion configured to change a form in the accommodation space between a first form in which the clamping portion clamps the medical device accommodated in the accommodation space and a second form in which the clamping portion does not clamp the medical device accommodated in the accommodation space. The movable portion engages the clamping portion to change the form of the clamping portion from the first form to the second form.

8 Claims, 15 Drawing Sheets

(56) References Cited

U.S. PATENT DOCUMENTS

| | | | |
|---|---|---|---|
| 2010/0174157 A1* | 7/2010 | Brister | A61B 5/72 600/309 |
| 2012/0253144 A1* | 10/2012 | Chin | A61B 5/14503 600/309 |
| 2013/0131467 A1 | 5/2013 | Deck et al. | |
| 2014/0243844 A1* | 8/2014 | Clancy | A61B 90/39 606/117 |
| 2015/0073238 A1* | 3/2015 | Matsumoto | A61B 5/1495 600/302 |
| 2016/0066953 A1* | 3/2016 | Minamiguchi | G01N 21/65 600/317 |
| 2016/0136357 A1 | 5/2016 | Yang | |
| 2017/0290533 A1 | 10/2017 | Antonio et al. | |
| 2017/0303831 A1 | 10/2017 | Tsubouchi et al. | |

FOREIGN PATENT DOCUMENTS

| | | |
|---|---|---|
| JP | 2012-205676 A | 10/2012 |
| JP | 2017-118911 A | 7/2017 |
| JP | 2019-507613 A | 3/2019 |
| WO | WO-2018/173467 A1 | 9/2018 |
| WO | WO-2019/045503 A1 | 3/2019 |

OTHER PUBLICATIONS

Chinese Office Action issued in connection with CN Appl. Ser. No. 202080014957.5 dated Mar. 3, 2023.

International Searching Authority, "Written Opinion," issued in connection with PCT Application No. PCT/JP2020/025091, dated Sep. 8, 2020 (6 pages).

International Searching Authority, "International Search Report," issued in connection with International Patent Application No. PCT/JP2020/025091, dated Sep. 8, 2020.

International Searching Authority, "Written Opinion," issued in connection with International Patent Application No. PCT/JP2020/025091, dated Sep. 8, 2020.

* cited by examiner

[FIG. 1]
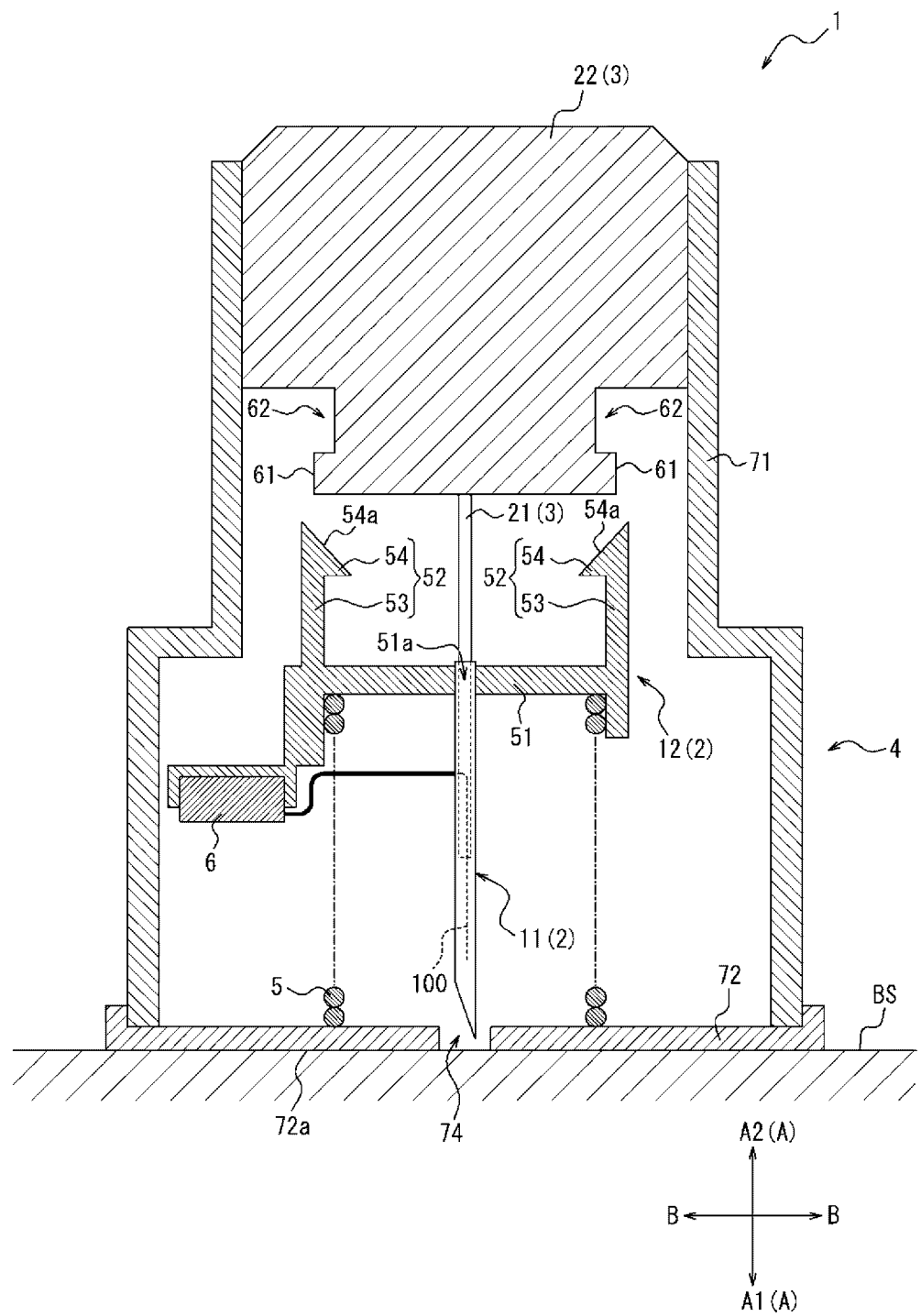

[FIG. 2]
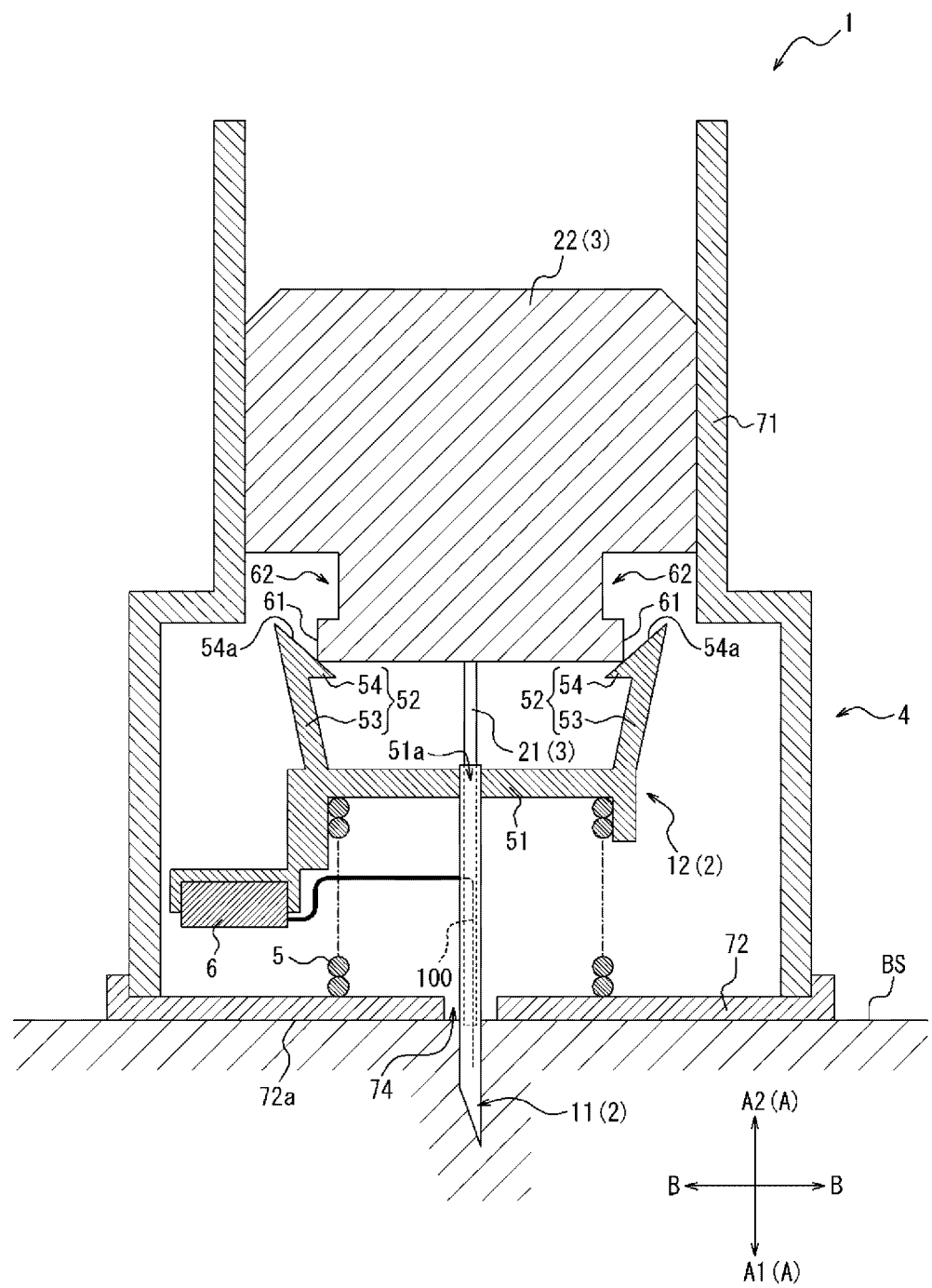

[FIG. 3]
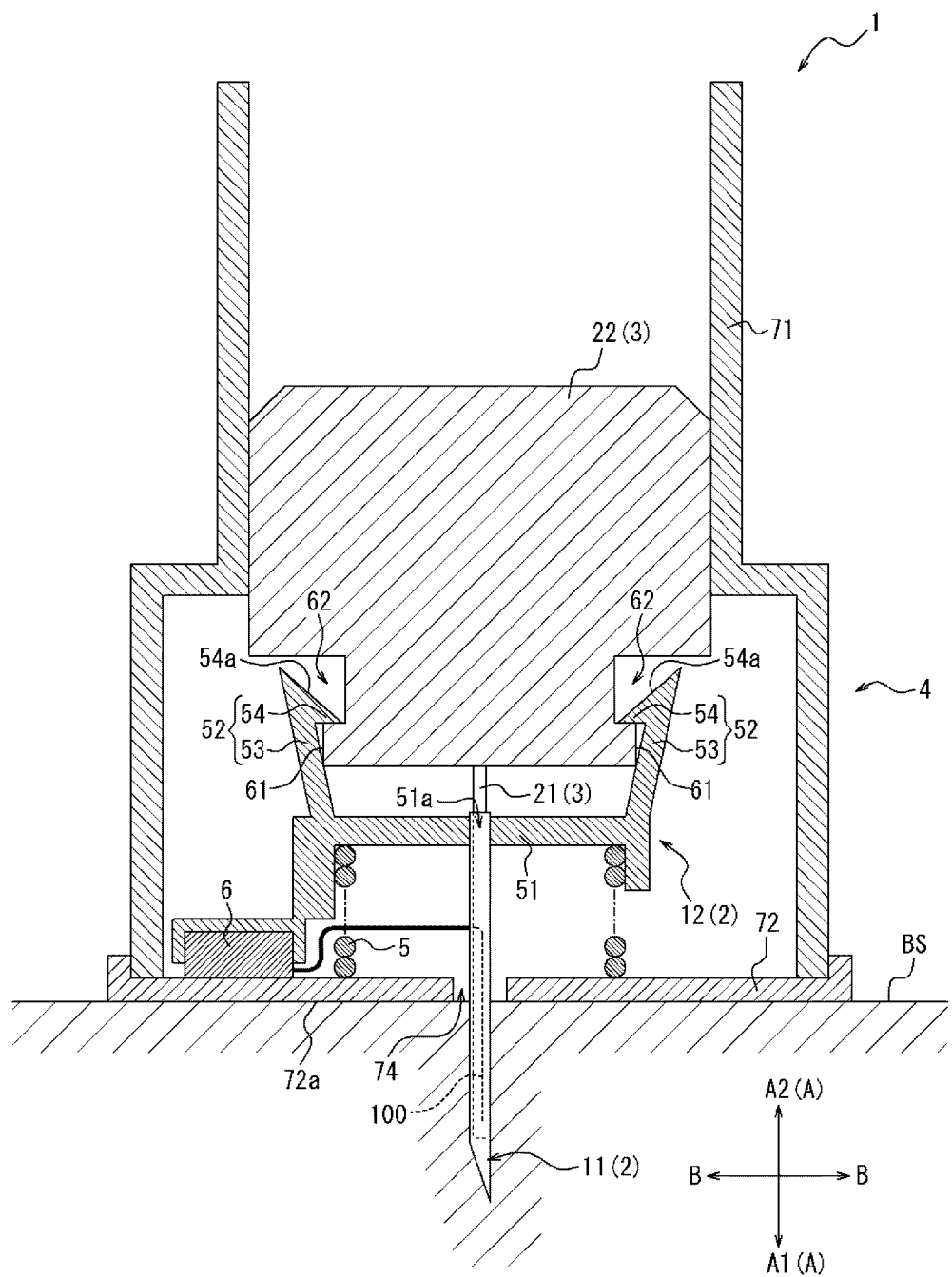

[FIG. 4]
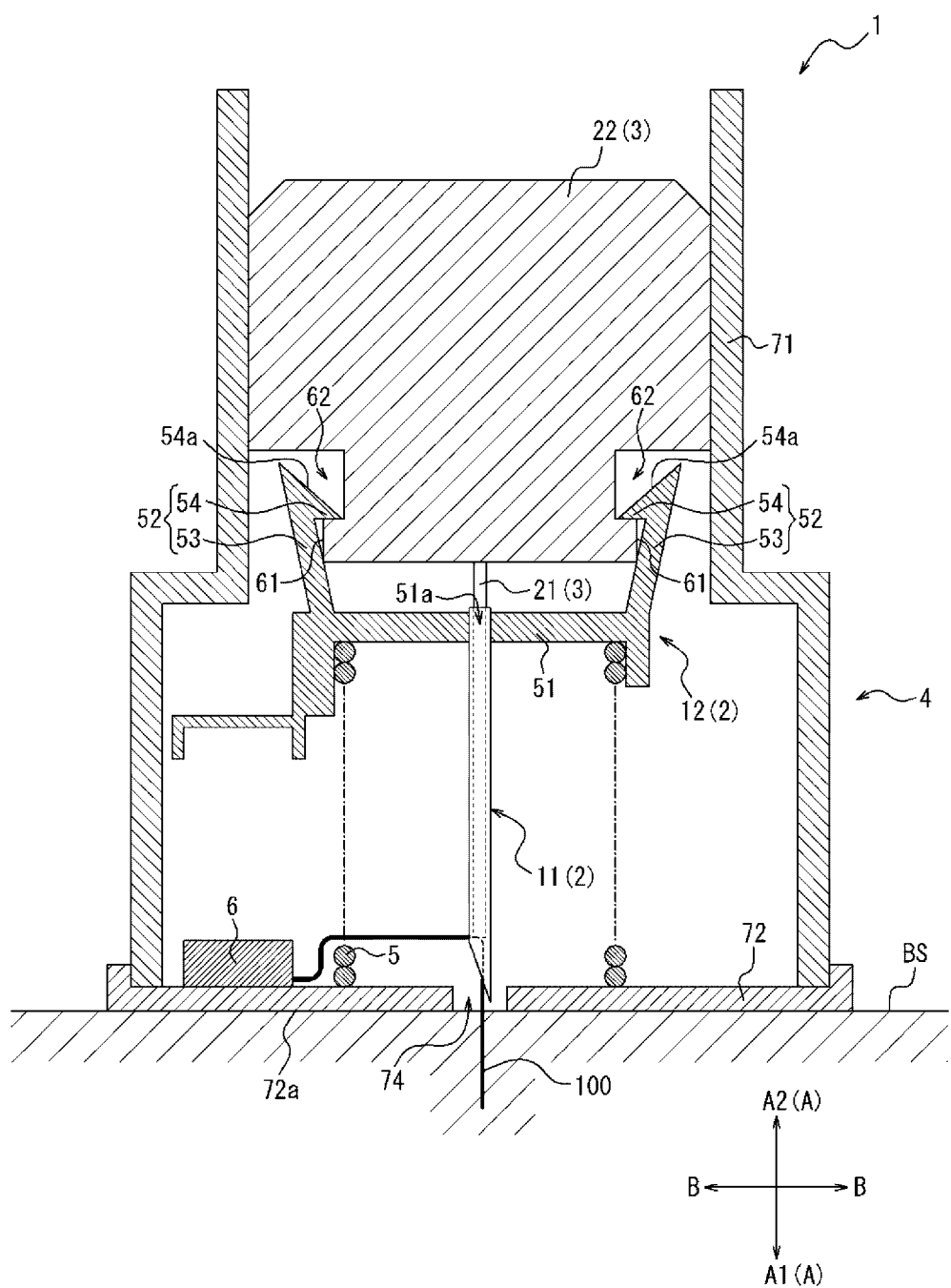

[FIG. 5A]
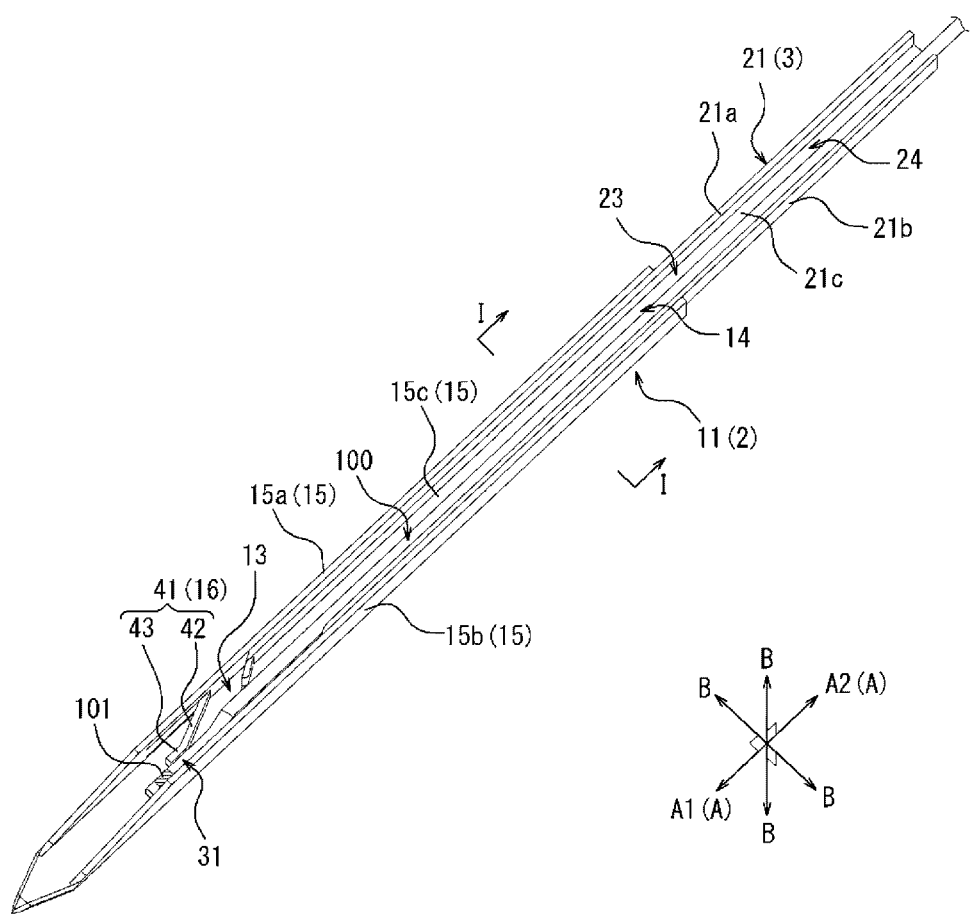

[FIG. 5B]
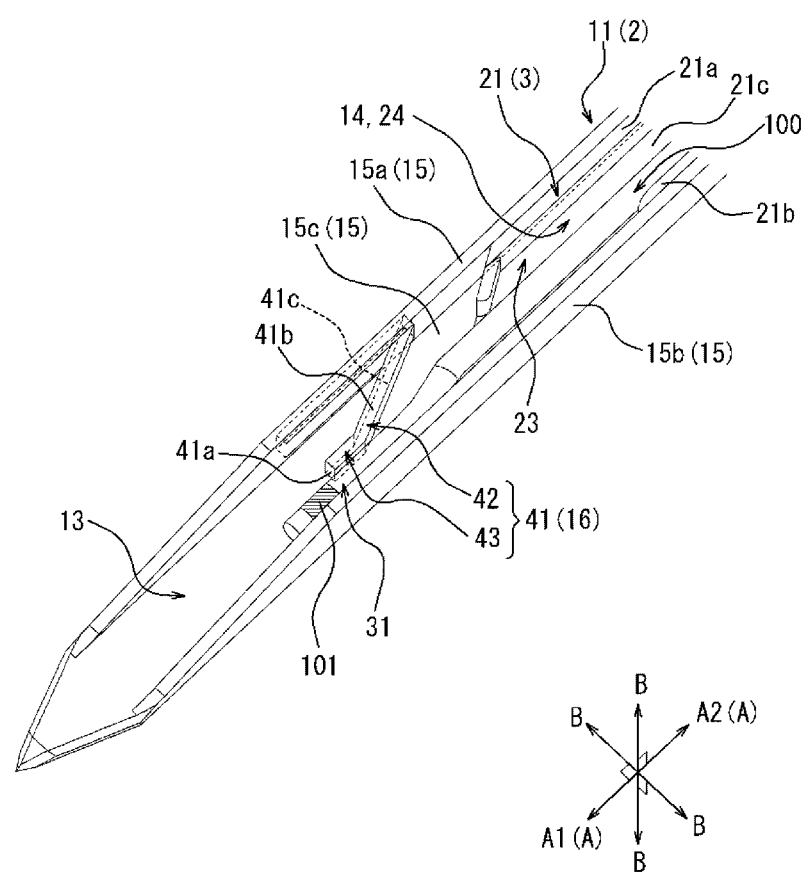

[FIG. 6A]
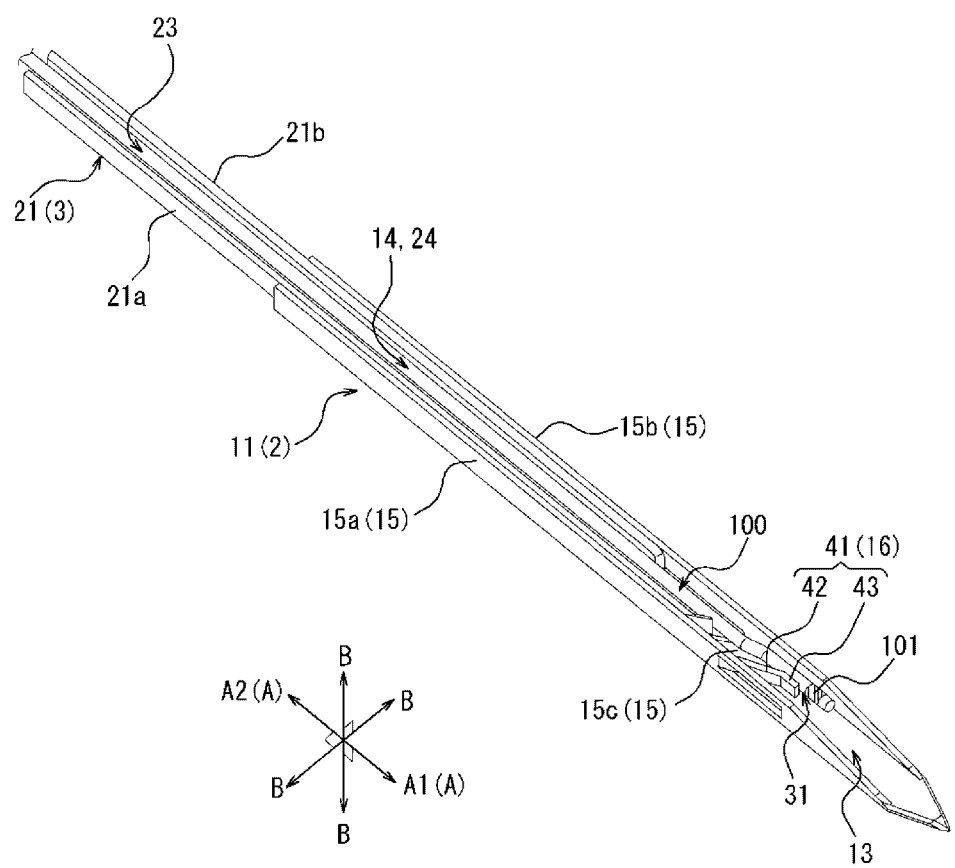

[FIG. 6B]
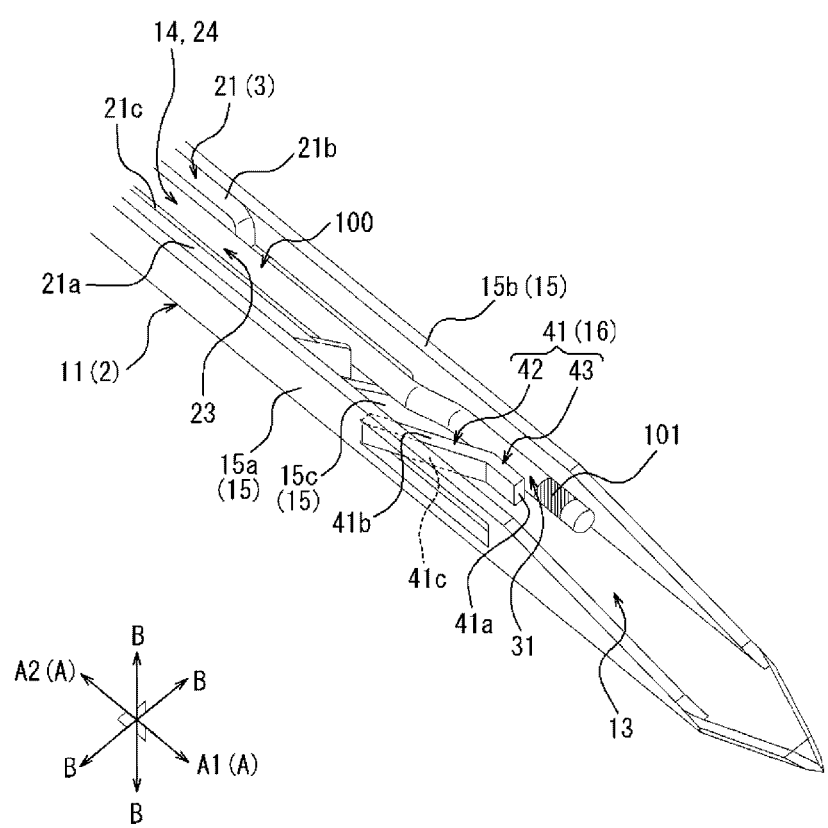

[FIG. 7]
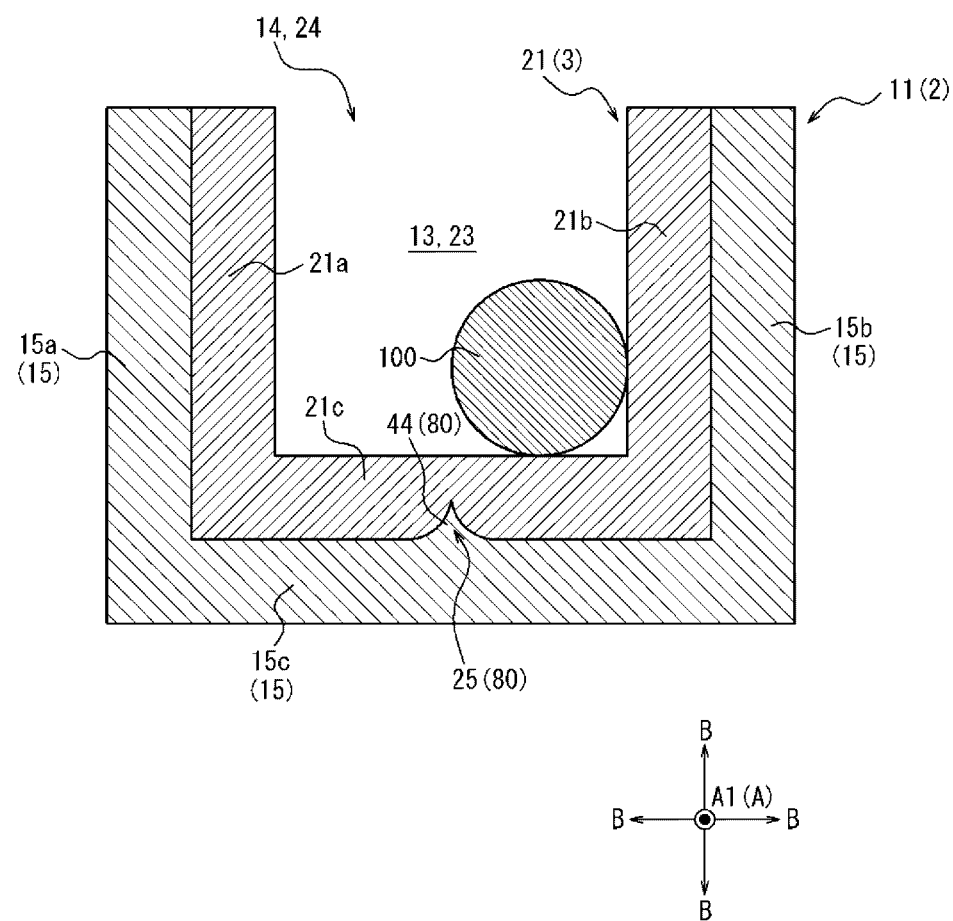

[FIG. 8A]
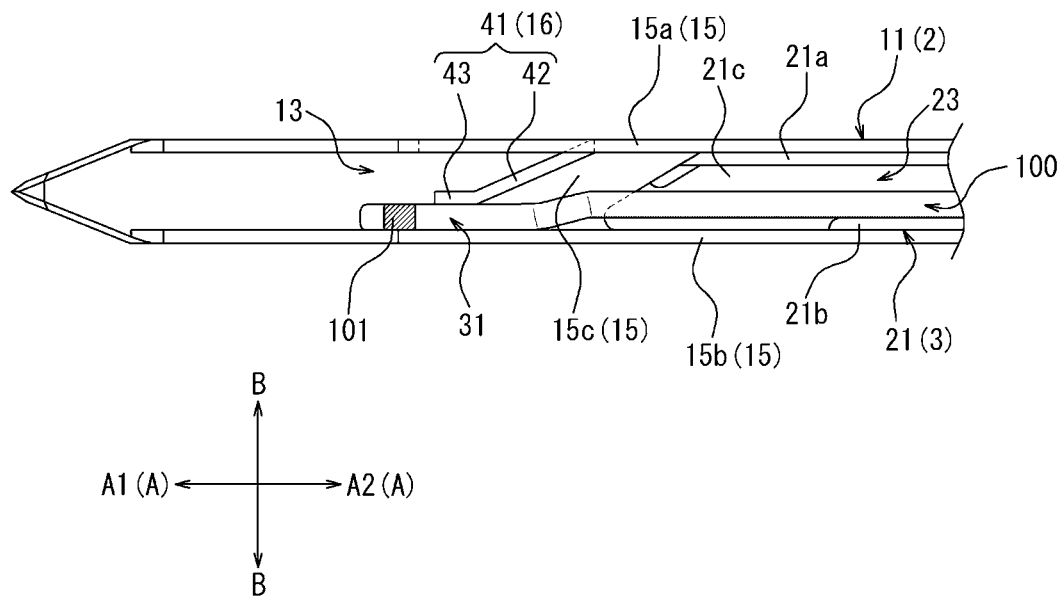
[FIG. 8B]
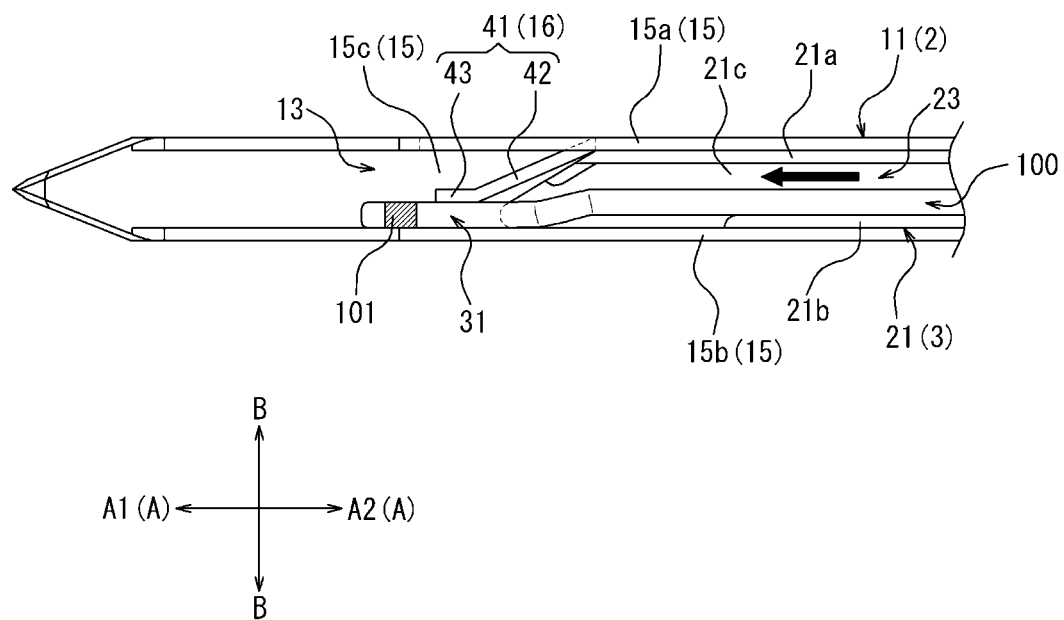

[FIG. 8C]
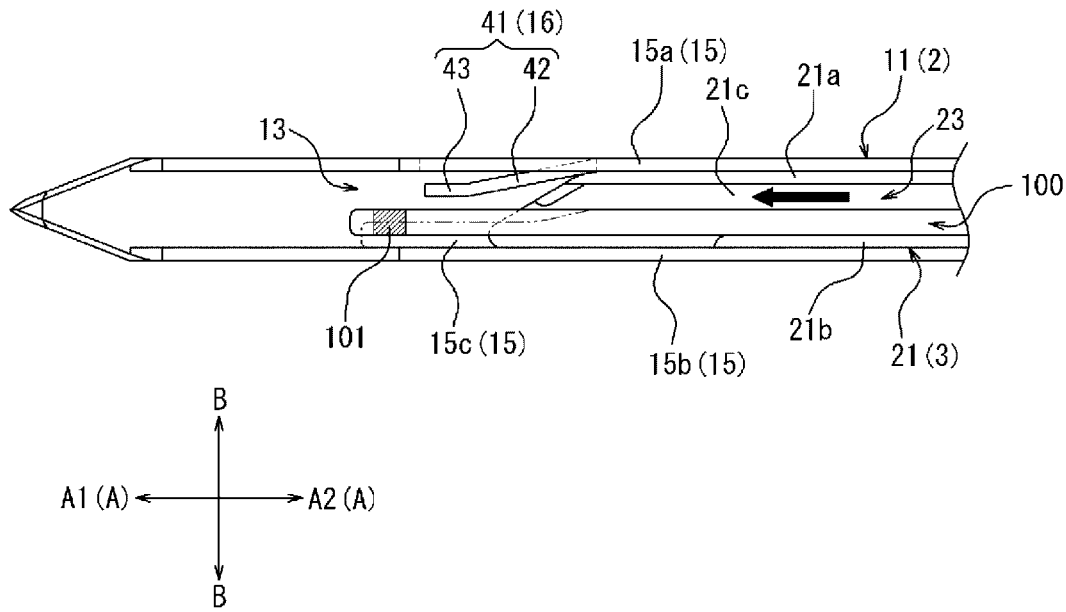
[FIG. 8D]
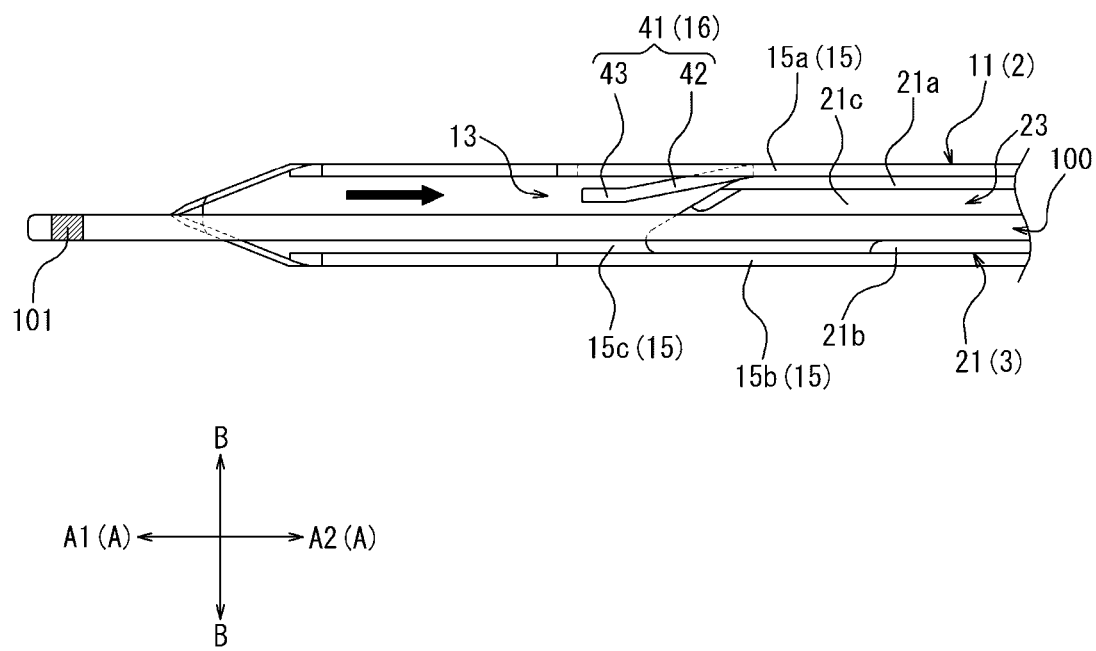

[FIG. 9]
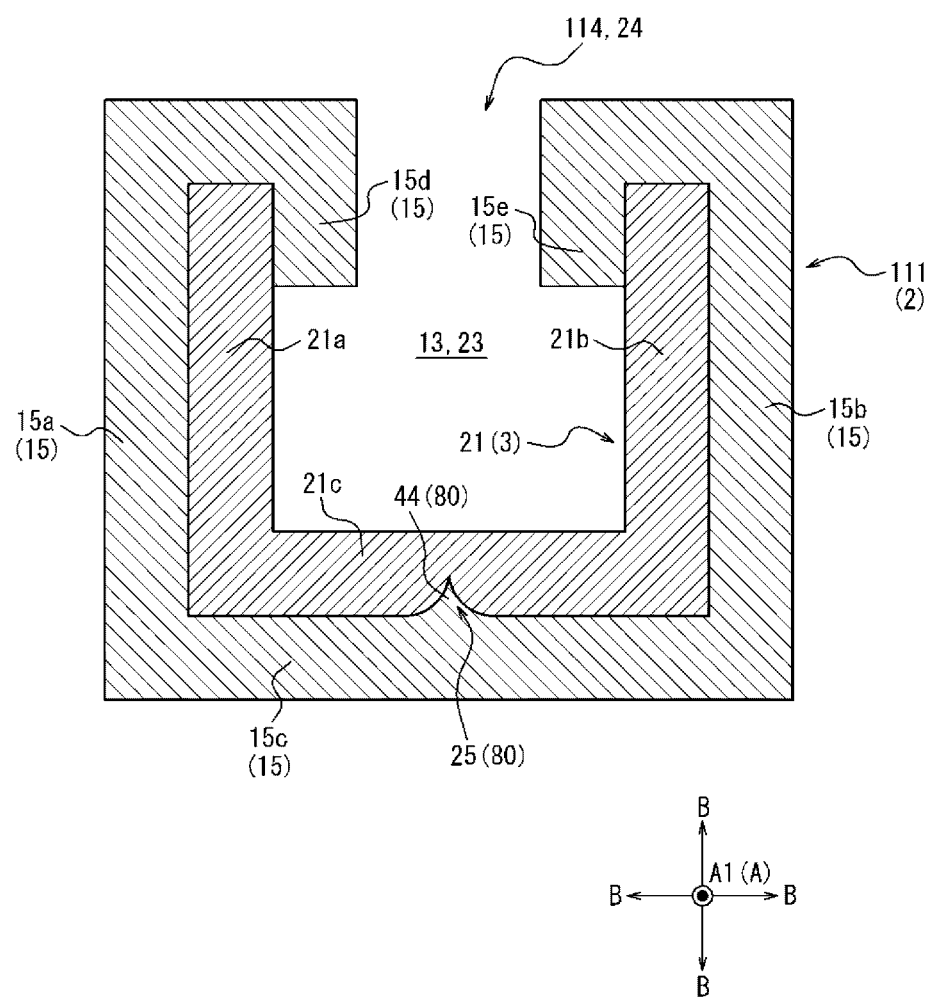

[FIG. 10]
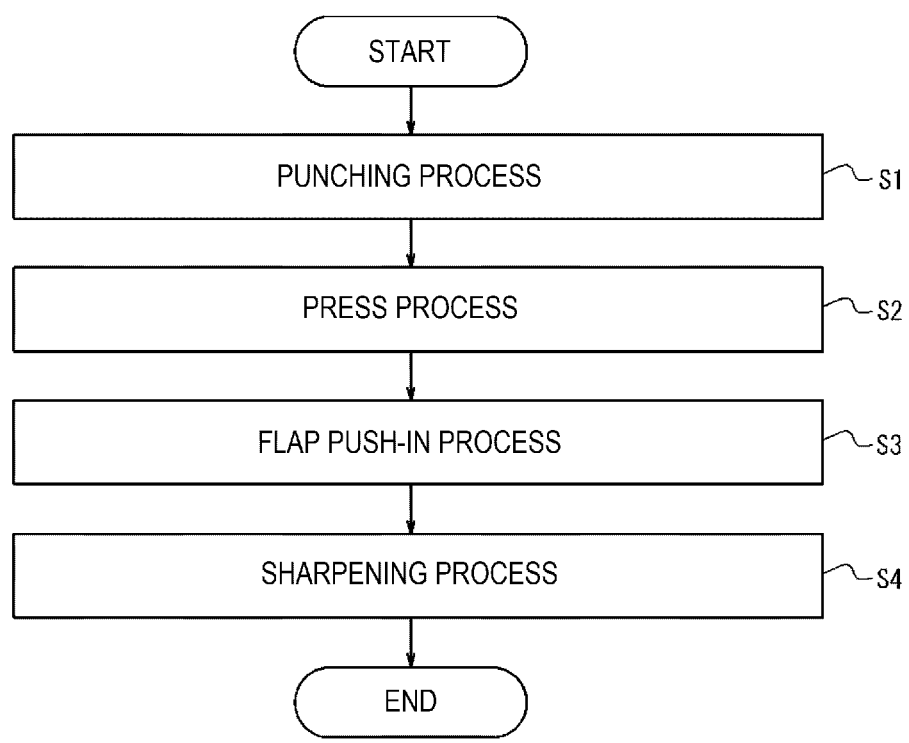

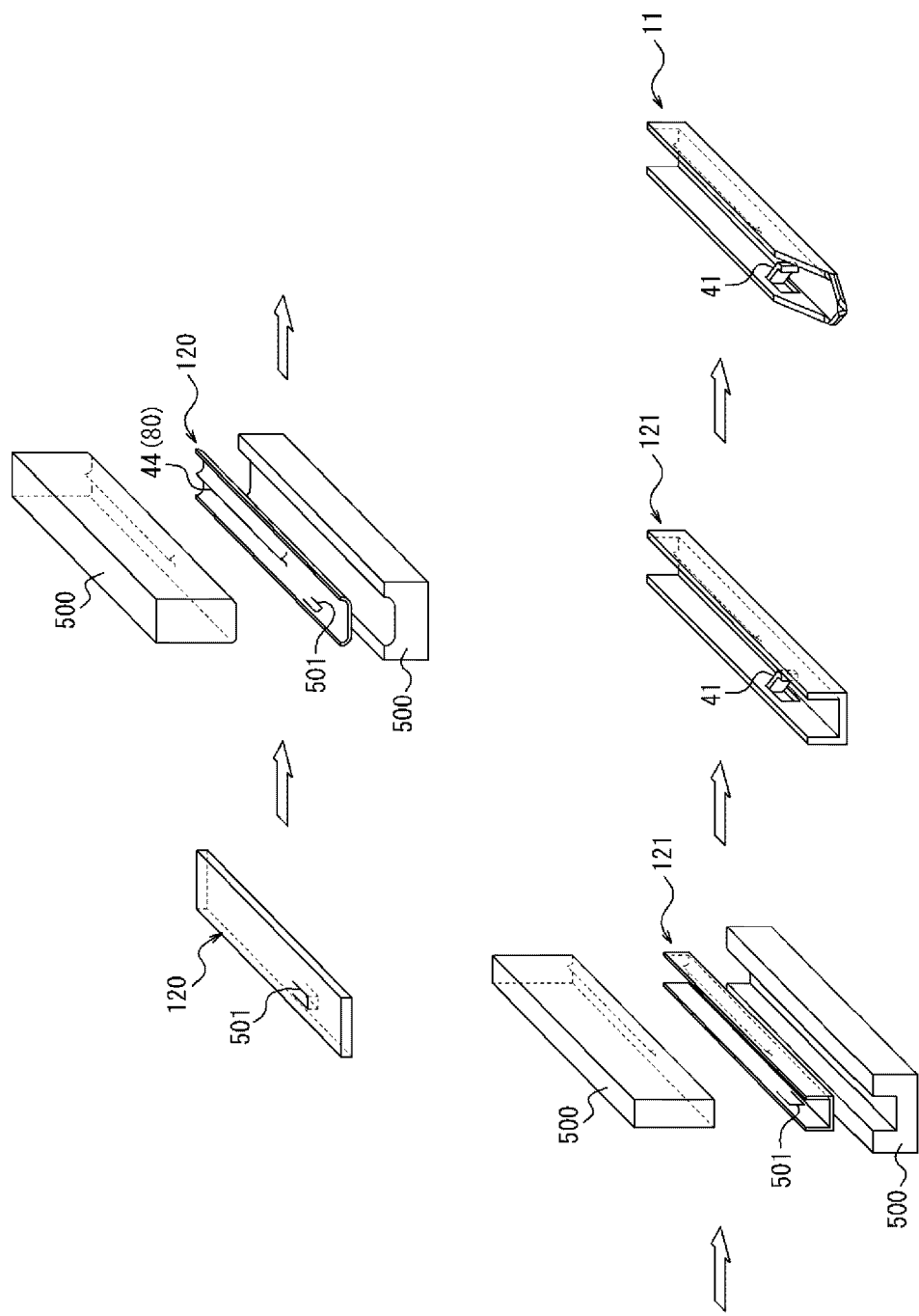
[FIG. 11]

[FIG. 12]
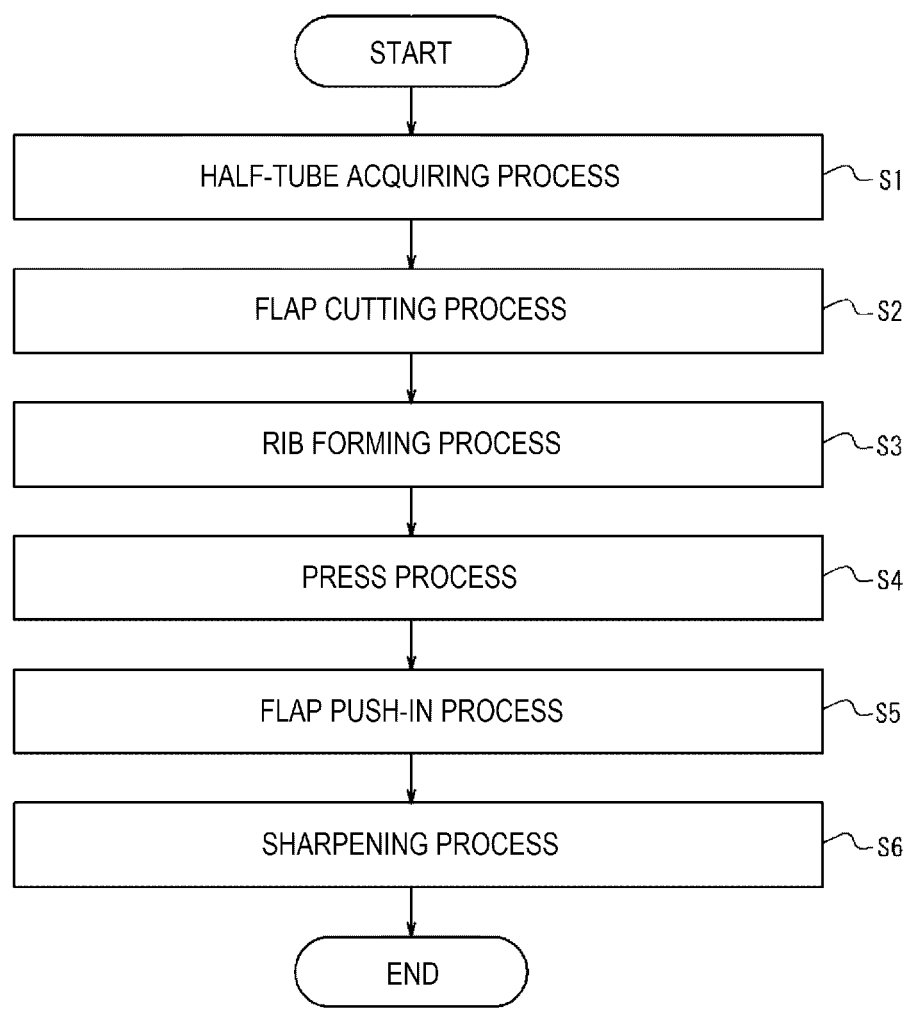

INSERTION DEVICE AND NEEDLE MEMBER

CROSS-REFERENCE TO RELATED APPLICATION

The present application is a bypass continuation of PCT Application No. PCT/JP2020/025091, filed on Jun. 25, 2020, which claims priority to Japanese Application No. 2019-142877, filed on Aug. 2, 2019. The contents of these applications are hereby incorporated by reference in their entireties.

BACKGROUND

The present disclosure relates to an insertion device and a needle member.

Conventionally, a medical device such as a tubular member, a sensor, and the like may be implanted in a living body of a subject such as a patient. In one example, a sensor is implanted in a living body of the subject and detection of analytes (for example, glucose, pH, cholesterol, protein, and the like) in blood or in a body fluid of the subject is performed. In this case, an insertion device is used to quickly and easily implant a sensor in the living body through the skin of the subject (see JP-T-2019-507613). The insertion device described in JP-T-2019-507613 is configured to insert the sensor into the living body together with a needle portion, implant the sensor, and then remove only the needle portion from the living body.

SUMMARY

When a gap between the needle portion and a medical device accommodated in the needle portion is small, the medical device is likely to be caught by an inner surface of the needle portion when removing the needle portion from the living body with the medical device remaining in the living body. Therefore, an insertion position of the medical device may be shallower than the desired depth in the living body. When the gap between the needle portion and the medical device accommodated in the needle portion is large, the medical device is likely to move in the needle portion due to an impact or the like when the medical device and the needle portion are inserted into the living body together. Therefore, the medical device may not be inserted at the desired depth in the living body.

The present disclosure is intended to provide an insertion device and a needle member provided with a needle portion configured to easily achieve implantation of a medical device at a desired depth in a living body.

According to a first embodiment, an insertion device for inserting a medical device into a living body includes: a needle portion internally defining an accommodation space that can accommodate the medical device and configured to be inserted into a living body together with the medical device to be accommodated in the accommodation space; and a movable portion relatively movable with respect to the needle portion in the accommodation space in a direction of insertion of the needle portion, wherein the needle portion includes a clamping portion capable of changing a form in the accommodation space between a first form of clamping the medical device accommodated in the accommodation space and a second form of not clamping the medical device accommodated in the accommodation space, and the movable portion engages the clamping portion by moving in the direction of insertion with respect to the needle portion to change the form of the clamping portion from the first form to the second form.

According to one aspect, the needle portion includes a sidewall portion that defines the accommodation space and a projection portion projecting from the sidewall portion toward the accommodation space, and the clamping portion includes an inner surface of the sidewall portion and the projection portion, the movable portion engages the projecting portion by moving in the direction of insertion with respect to the needle portion and deforming the projection portion to change the form of the clamping portion from the first form to the second form.

According to another aspect, the movable portion defines a groove space extending along the direction of insertion that is located within the accommodation space and can accommodate the medical device.

According to another aspect, the insertion device includes a restricting mechanism configured to restrict relative movement of the needle portion and the movable portion in directions other than a longitudinal direction of the needle portion.

According to another embodiment, a needle member internally defines an accommodation space that can accommodate the medical device and includes a needle portion configured to be inserted into a living body together with a medical device to be accommodated in the accommodation space. The needle portion includes a clamping portion located in the accommodation space and capable of changing a form between a first form of clamping the medical device accommodated in the accommodation space and a second form of not clamping the medical device accommodated in the accommodation space.

According to certain embodiments of the present disclosure, an insertion device and a needle member including a needle portion configured to easily achieve implantation of a medical device at the desired depth in a living body is provided.

BRIEF DESCRIPTION OF THE DRAWINGS

FIG. 1 is a drawing illustrating an insertion device according to an embodiment of the present disclosure and a state in which a needle portion is located in a waiting position.

FIG. 2 is a drawing illustrating a state in which the needle portion of the insertion device illustrated in FIG. 1 is in the course of moving from the waiting position to an insertion position.

FIG. 3 is a drawing illustrating a state in which the needle portion of the insertion device illustrated in FIG. 1 is in the insertion position.

FIG. 4 is a drawing illustrating a state in which the needle portion of the insertion device illustrated in FIG. 1 is removed from the insertion position to outside of a living body.

FIG. 5A is a perspective view illustrating the needle portion, a movable portion, and a sensor in the insertion device in the state illustrated in FIG. 1.

FIG. 5B is an enlarged perspective view illustrating a vicinity of a distal end portion of the needle portion in FIG. 5A in an enlarged scale.

FIG. 6A is a perspective view illustrating the needle portion, the movable portion, and the sensor in the insertion device in the state illustrated in FIG. 1, viewed from a viewpoint different from FIG. 5A.

FIG. 6B is an enlarged perspective view illustrating a vicinity of a distal end portion of the needle portion in FIG. 6A in an enlarged scale.

FIG. 7 is a cross-sectional view taken along a section along a line I-I in FIG. 5A.

FIG. 8A is a drawing illustrating the needle portion, the movable portion and the sensor in the state in which the needle portion of the insertion device illustrated in FIG. 1 is in the waiting position.

FIG. 8B is a drawing illustrating the needle portion, the movable portion and the sensor in the state in which the needle portion of the insertion device illustrated in FIG. 1 is in the course of moving from the waiting position to the insertion position.

FIG. 8C is a drawing illustrating the needle portion, the movable portion and the sensor in the state in which the needle portion of the insertion device illustrated in FIG. 1 is in the insertion position.

FIG. 8D is a drawing illustrating the needle portion, the movable portion, and the sensor in the course of moving back into a housing after the needle portion of the insertion device illustrated in FIG. 1 has implanted the sensor at the insertion position.

FIG. 9 is a drawing illustrating a needle portion as a modification of the needle portion illustrated in FIG. 7.

FIG. 10 is a flowchart illustrating an example of a method of manufacturing the needle portion of the insertion device illustrated in FIG. 1.

FIG. 11 is a drawing illustrating an overview of respective processes of the method of manufacturing illustrated in FIG. 10.

FIG. 12 is a flowchart illustrating a modification of a method of manufacturing the needle portion illustrated in FIG. 10.

DETAILED DESCRIPTION

Referring now to the drawings, embodiments of an insertion device and a needle member according to the present disclosure will be described. The same reference numerals are given to common parts and portions in the drawings.

FIG. 1 to FIG. 4 illustrate an insertion device 1 according to a first embodiment of the present disclosure. In addition, as will be described in detail below, FIG. 1 to FIG. 4 each illustrate an overview of an operation of the insertion device 1 when inserting and implanting a sensor 100 in a living body using the insertion device 1. The insertion device 1 illustrated in FIG. 1 to FIG. 4 can insert the sensor 100 as the medical device into the living body. Hereinafter, in the present embodiment, the insertion device 1 configured to insert the sensor 100 into the living body will be described. However, the medical device to be inserted into the living body by the insertion device 1 is not limited to the sensor 100. Therefore, the insertion device may be configured to insert a tubular member other than the sensor, such as a cannula.

As illustrated in FIG. 1 to FIG. 4, the insertion device 1 includes a needle member 2, a movable member 3, a housing 4, a biasing member 5, a controller 6, and the sensor 100. As will be described in detail below, the needle member 2 of the present embodiment includes a needle portion 11. Also, as will be described in detail below, the movable member 3 of the present embodiment includes a movable portion 21.

Referring now to FIG. 1 to FIG. 4, a method of using the insertion device 1 of the present embodiment will be described. The insertion device 1 of the present embodiment may be used for inserting and implanting the sensor 100 in the living body as described above. The insertion device 1 is disposed on a living body surface BS in a state illustrated in FIG. 1. In other words, FIG. 1 illustrates a state before the needle portion 11 of the needle member 2 and the sensor 100 are inserted into a living body. Then, an operator such as a health care worker operates the insertion device 1 to insert the needle portion 11 of the needle member 2 and the sensor 100 into the living body (See FIG. 2 and FIG. 3). FIG. 2 is a drawing illustrating a state in the course of inserting the needle portion 11 and the sensor 100 into the living body by the insertion device 1. FIG. 3 is a drawing illustrating a state in which the needle portion 11 and the sensor 100 reach the deepest possible position in the living body where the insertion device 1 can be inserted. Next, as illustrated in FIG. 4, the needle portion 11 of the needle member 2 is removed to outside of the living body with the sensor 100 left in the living body. In this manner, the sensor 100 can be inserted and implanted into the living body by the insertion device 1. For the sake of convenience of explanation, the position of the needle portion 11 in FIG. 1 where the needle portion 11 is accommodated in the housing 4 may be referred to as "a (the) waiting position of the needle portion 11" hereinafter. Likewise, for the sake of convenience of explanation, the position of the needle portion 11 in FIG. 3 where the needle portion 11 protrudes the most from the housing 4 is referred to as "a (the) insertion position of the needle portion 11" hereinafter.

The sensor 100 to be implanted in the living body detects a substance to be measured (analyte) and transmits information of a detection result to the controller 6. The controller 6 is connected to the sensor 100 and is implanted on the living body surface BS together with the sensor 100. The controller 6 includes a processor, a memory, a battery, a communication unit and the like. The sensor 100 of the present embodiment illustrated in FIG. 1 to FIG. 4 transmits the information of the detection result to the controller 6. By using the sensor 100 together with the controller 6, a signal can be detected according to the concentration of the substance to be measured. The detected signal is processed by the controller 6 and is transmitted to a smartphone or a dedicated terminal of a subject. The subject or the user can confirm the result of measurement of the substance to be measured displayed on a screen of the smartphone or the dedicated terminal with time. A time period during which the sensor 100 is attached to the subject is determined as appropriate in the determination of the doctor or the like, such as several hours, several days, a week, a month, and so forth. Although the substance to be measured is not particularly limited, for example, glucose, oxygen, pH, lactic acid, or the like in the blood or an interstitial fluid can be measured according to the selection of the detection portion of the sensor 100. Note that the controller 6 may be connected to a separately provided transmitter (not illustrated) after the completion of insertion of the sensor 100. In this case, instead of the controller 6, the transmitter may be configured to have a memory, a battery, and the like. The transmitter may be configured to be used for a longer period than the sensor 100.

The details of each member and each portion of the insertion device 1 will be described below.

FIG. 5A and FIG. 6A are perspective views illustrating the needle portion 11 of the needle member 2, the movable portion 21 of the movable member 3, and the sensor 100 in the insertion device 1 in the state illustrated in FIG. 1. FIG. 5A and FIG. 6A are perspective views viewed from different viewpoints. FIG. 5B is an enlarged perspective view illustrating a vicinity of a distal end portion of the needle portion 11 in FIG. 5A in an enlarged scale. FIG. 6B is an enlarged perspective view illustrating the vicinity of the distal end portion of the needle portion 11 in FIG. 6A in an enlarged scale.

Hereinafter, in this specification, an end of the needle portion 11 of the needle member 2 to be inserted into the living body will be referred to as "a (the) distal end of the needle portion 11." Also, an opposite end from the distal end of the needle portion 11 of the needle member 2 is referred to as "a (the) proximal end of the needle portion 11." Further, a direction from the proximal end toward the distal end of a longitudinal direction A of the needle portion 11 of the needle member 2 is referred to as "direction of insertion A1" or "distal side." Further, a direction from the distal end toward the proximal end of the longitudinal direction A of the needle portion 11 of the needle member 2 is referred to as "direction of removal A2" or "proximal side." A radial direction B of the needle portion 11 refers to a radial direction of a circle, which is defined on a plane orthogonal to the longitudinal direction A of the needle portion 11 around the needle portion 11 with a center at the needle portion 11. An outward direction from a central axis of the needle portion 11 of the needle member 2 is referred to as "outward in the radial direction B." A direction toward the central axis of the needle portion 11 from a circumference of the circle, which is defined around the needle portion 11 of the needle member 2, is referred to as "inside in the radial direction B." The center of the circle is an equal distance from one end portion (connection with the first side plate portion 15a) and the other end (connection with the second side plate portion 15b) of the third side plate portion 15c described below in the cross section in the short axis direction of the needle portion 11.

As illustrated in FIG. 1 to FIG. 4, the needle member 2 includes the needle portion 11 and a holding portion 12.

As illustrated in FIG. 1 to FIG. 6, the needle portion 11 internally includes an accommodation space 13 that can accommodate the sensor 100. The needle portion 11 is inserted into the living body together with the sensor 100 to be accommodated in the accommodation space 13.

As illustrated in FIG. 5A, FIG. 5B, FIG. 6A, and FIG. 6B, the needle portion 11 includes a clamping portion 31 capable of clamping the sensor 100 accommodated in the accommodation space 13. A form of the clamping portion 31 in the accommodation space 13 changes between a first form of clamping the sensor 100 accommodated in the accommodation space 13 and a second form of not clamping the sensor 100 accommodated in the accommodation space 13. A form of the clamping portion 31 changes from the first form to the second form by engaging the movable portion 21, described below. In this manner, the needle portion 11 configured to achieve implantation of the sensor 100 at the desired depth easily in the living body is realized. Details of the change of the form of the clamping portion 31 of the present embodiment will be described below (see FIG. 8A to FIG. 8D).

As illustrated in FIG. 5A, FIG. 5B, FIG. 6A, and FIG. 6B, the needle portion 11 of the present embodiment is provided with a gap 14 formed to extend in a longitudinal direction A. The gap 14 may be formed over an entire area of the needle portion 11 in the longitudinal direction A as in the present embodiment. Alternatively, the gap 14 may be formed only in part of the needle portion 11 in the longitudinal direction A. However, when the gap 14 is formed only in part of the needle portion 11 in the longitudinal direction A, the gap 14 extends at least from the middle of the needle portion 11 in the longitudinal direction A to a distal end of the needle portion 11. In other words, the gap 14 is opened to outside at the distal end of the needle portion 11. The length of the gap 14 in the longitudinal direction A is not specifically limited. The length may be designed as needed according to the length of the sensor 100, described below, or the like.

As illustrated in FIG. 5A, FIG. 5B, FIG. 6A, and FIG. 6B, the needle portion 11 of the present embodiment includes a sidewall portion 15 that defines the accommodation space 13 and a projection portion 16 projecting from the sidewall portion 15 toward the accommodation space 13.

The sidewall portion 15 of the present embodiment includes the first side plate portion 15a and the second side plate portion 15b arranged to face each other, and the third side plate portion 15c continuing to the respective end portions of the first side plate portion 15a and the second side plate portion 15b on one side. The first side plate portion 15a, the second side plate portion 15b, and the third side plate portion 15c define the accommodation space 13. The gap 14 described above is formed at a position opposing the third side plate portion 15c with the accommodation space 13 interposed therebetween. That is, a space interposed between the first side plate portion 15a and the second side plate portion 15b on an upper side of the third side plate portion 15c of the needle portion 11 corresponds to the accommodation space 13.

The sidewall portion 15 extends in the longitudinal direction A. More specifically, the first side plate portion 15a, the second side plate portion 15b, and the third side plate portion 15c of the present embodiment are each made of an elongated flat plate portion extending in the longitudinal direction A. That is, the sidewall portion 15 of the present embodiment monolithically defines a rectangular-shaped groove with three flat-plate shaped portions: the first side plate portion 15a, the second side plate portion 15b, and the third side plate portion 15c. However, the cross-sectional profile orthogonal to the longitudinal direction A of the sidewall portion 15 is not limited to the shape of the rectangular-shaped groove as in the present embodiment. Rather, the sidewall portion 15 may have other cross-sectional profiles, such as a U-shape, C-shape, and the like. In that case, the first side plate portion 15a and the second side plate portion 15b have a flat-plate shape, and the third side plate portion 15c is a half-tubular member having a cross-sectional shape of a semicircular shape or a substantially half semicircular arc. In this manner, the needle portion 11 has the gap 14 at a position opposing the third side plate portion 15c, and the gap 14 extends in the longitudinal direction A of the needle portion 11. Because the sensor 100 of the present embodiment is connected to the controller 6 via a wire, the sidewall portion 15 is configured to have the gap 14. In the case of the sensor or the like connected to the controller 6 wirelessly, a tubular sidewall portion having no gap 14 is also applicable.

However, as will be described in detail below, when a flap 41 is formed by using part of the sidewall portion 15 and the flap 41 is utilized as the projection portion 16 (see FIG. 6B, etc.), it is preferable to provide a flat-plate shaped portion on at least a portion of the sidewall portion 15 provided with the flap 41. In this configuration, the resiliently deforming performance of the flap 41 as the projection portion 16 may be enhanced.

As illustrated in FIG. 5A, FIG. 5B, FIG. 6A, and FIG. 6B, a cutting edge is formed at a distal end of the sidewall portion 15. In the sidewall portion 15 of the present embodiment, the third side plate portion 15c extends further in a direction of insertion A1 than does a distal end portion of the first side plate portion 15a and the second side plate portion 15*b*. In the sidewall portion 15 of the present embodiment, the cutting edge is formed only at a distal end of the third side plate portion 15*c*. More specifically, the distal end portion of the flat-plate shaped third side plate portion 15*c* of the present embodiment is provided with a tapered portion on both sides in a width direction so as to be tapered toward the distal end. Accordingly, the distal end of the third side plate portion 15*c* is sharpened to form the cutting edge of the sidewall portion 15. At the distal end portion of the third side plate portion 15*c*, distal end surfaces of the first side plate portion 15*a* and the second side plate portion 15*b* in the direction of insertion A1 are inclined with respect to the longitudinal direction A so that end surfaces of the first side plate portion 15*a* and the second side plate portion 15*b* along the gap 14 get closer to the third side plate portion 15*c* as it proceeds in the direction of insertion A1. In the present embodiment, although the distal end of the third side plate portion 15*c* is sharpened to form the cutting edge of the sidewall portion 15, the configuration is not limited thereto. For example, the sidewall portion may have such configuration that the distal end surface includes one or more cutting surfaces that incline with respect to the longitudinal direction A.

In the present embodiment, facing widths of outer surfaces of the first side plate portion 15*a* and the second side plate portion 15*b* of the sidewall portion 15 may be, for example, 0.2 mm to 0.6 mm. A length of the sidewall portion 15 to be inserted into the living body may be, for example, 1 mm to 10 mm, preferably 3 to 6 mm. A thickness of the first side plate portion 15*a*, the second side plate portion 15*b*, and the third side plate portion 15*c* may be set from a range, for example, from 0.02 mm to 0.15 mm.

As illustrated in FIG. 5A, FIG. 5B, FIG. 6A, and FIG. 6B, the projection portion 16 projects from the sidewall portion 15 toward the accommodation space 13 as described above. The projection portion 16 of the present embodiment projects from the first side plate portion 15*a* of the sidewall portion 15 toward the accommodation space 13. However, the projection portion 16 may project from the second side plate portion 15*b* or the third side plate portion 15*c* toward the accommodation space 13.

Also, as illustrated in FIG. 5A, FIG. 5B, FIG. 6A, and FIG. 6B, the projection portion 16 of the present embodiment is formed of the flap 41 formed on part of the sidewall portion 15. When the flap 41 as the projecting portion 16 of the present embodiment is pushed toward the accommodation space 13, a distal side of the flap projects toward the accommodation space 13. More specifically, the flap 41 as the projection portion 16 of the present embodiment is formed by forming a slit in the first side plate portion 15*a* and pushing toward the accommodation space 13. In this manner, the projection portion 16 is achieved with a simple configuration.

The flap 41 as the projection portion 16 of the present embodiment includes a first outer edge portion 41*a*, a second outer edge portion 41*b*, and a third outer edge portion 41*c*. The first outer edge portion 41*a* extends linearly in a direction orthogonal to the longitudinal direction A in the first side plate portion 15*a*. The second outer edge portion 41*b* extends linearly or in a curved manner from one end of the first outer edge portion 41*a* (the gap 14 side of the needle portion 11 in the present embodiment) to one end side of the longitudinal direction A (a direction of removal A2 in the present embodiment). The third outer edge portion 41*c* extends linearly or in a curved manner from the other end of the first outer edge portion 41*a* (the third side plate portion 15*c* side in the present embodiment) to one end side of the longitudinal direction A (the direction of removal A2 in the present embodiment). The flap 41 as the projection portion 16 of the present embodiment is formed by the first outer edge portion 41*a*, the second outer edge portion 41*b*, and the third outer edge portion 41*c*. In other words, the flap 41 of the present embodiment has an end portion in the direction of removal A2 continuing to the first side plate portion 15*a* of the sidewall portion 15. The flap 41 of the present embodiment is pushed at the end portion side in the direction of insertion A1 toward the accommodation space 13 with an end portion in the direction of removal A2, which continues to the first side plate portion 15*a*, as a fulcrum. Specifically, the flap 41 of the present embodiment includes an inclined portion 42 inclining with respect to the longitudinal direction A away from the first side plate portion 15*a* toward the interior of the accommodation space 13 as it goes from the end portion continuing to the first side plate portion 15*a* in the direction of removal A2 toward a free end in the direction of insertion A1. In other words, the inclined portion 42 inclines from the first side plate portion 15*a* in a direction toward the second side plate portion 15*b* as it goes to the free end in the direction of insertion A1. In addition, the flap 41 of the present embodiment includes, in addition to the inclined portion 42 described above, a flap distal end portion 43 continuing to the inclined portion 42. The flap distal end portion 43 of the present embodiment has a smaller angle of inclination with respect to the longitudinal direction A than the inclined portion 42. The flap distal end portion 43 of the present embodiment extends substantially parallel to the longitudinal direction A.

As described above, all of the first outer edge portion 41*a*, the second outer edge portion 41*b*, and the third outer edge portion 41*c* extend linearly. In other words, the flap 41 as the projection portion 16 of the present embodiment has a substantially rectangular profile. However, the shape of the flap 41 as the projection portion 16 is not specifically limited. The flap 41 may have other profiles such as a U-shape, a C-shape, and a triangular shape.

Although the flap 41 as the projection portion 16 of the present embodiment includes the end portion in the direction of removal A2 continuing to the sidewall portion 15, the position of continuing to the sidewall portion 15 is not specifically limited. Therefore, the flap 41 may have the end portion in the direction of insertion A1 continuing to the sidewall portion 15. The flap 41 may be such that any of the end portions in the direction orthogonal to the longitudinal direction A continues to the sidewall portion 15. As will be described in detail below, the flap 41 as the projection portion 16 of the present embodiment clamps the sensor 100 between the flap 14 and an inner surface of the sidewall portion 15. Further, the flap 41 of the present embodiment is deformed by engaging the movable portion 21 that moves in the direction of insertion A1 within the accommodation space 13 to release the clamped state of the sensor 100. For these reasons, the flap 41 as the projection portion 16 is preferably configured to have the end portion in the direction of removal A2 continuing to the sidewall portion 15 as in the present embodiment. With the flap 41 configured in this manner, both of clamping of the sensor 100 described above and deformation by the engagement with the movable portion 21 moving in the direction of insertion A1 can easily be achieved with a simple form.

The clamping portion 31 of the needle portion 11 of the present embodiment includes the inner surface of the sidewall portion 15 and the projection portion 16. That is, the needle portion 11 of the insertion device 1 of the present embodiment clamps the sensor 100 to be accommodated in the accommodation space 13 between the inner surface of the sidewall portion 15 and the projection portion 16. More specifically, the needle portion 11 of the insertion device 1 of the present embodiment clamps the sensor 100 to be accommodated in the accommodation space 13 between the inner surface of the second side plate portion 15b of the sidewall portion 15 on the accommodation space 13 side and the flap distal end portion 43 of the flap 41 as the projection portion 16. The movable portion 21 of the movable member 3 described below moves in the accommodation space 13 in the direction of insertion A1 to engage the inclined portion 42 of the flap 41 as the projection portion 16. More in detail, the distal end of the movable portion 21 comes into contact with the flap 41 as the projection portion 16, and the movable portion 21 moves further in the direction of insertion A1, whereby the distal end portion of the movable portion 21 pushes the flap 41 away. Accordingly, the flap 41 as the projection portion 16 is resiliently deformed toward the first side plate portion 15a and is retracted from the interior of the accommodation space 13. In other words, the flap 41 as the projection portion 16 retracts away from the inner surface of the second side plate portion 15b of the sidewall portion 15 that clamps the sensor 100 together. Therefore, the clamped state of the sensor 100 between the inner surface of the second side plate portion 15b of the sidewall portion 15 and the flap 41 as the projection portion 16 is released. Consequently, the sensor 100 is brought into a state of movable in the longitudinal direction A with respect to the needle portion 11. This will be described in detail below (See FIG. 8A to FIG. 8D).

FIG. 7 is a cross-sectional view taken along a section along the line I-I in FIG. 5A. As illustrated in FIG. 7, the inner surface of the needle portion 11 of the present embodiment includes a rib 44 projecting toward the accommodation space 13. More specifically, the rib 44 protruding toward the accommodation space 13 and extending in the longitudinal direction A is formed on the inner surface of the third side plate portion 15c of the sidewall portion 15 of the needle portion 11 of the present embodiment. The rib 44 fits a receiving groove 25 of the movable portion 21 of the movable member 3, described below, and constitutes part of a restricting mechanism 80 together with the receiving groove 25. The rib 44 may simply be provided at least part of the needle portion 11 in the longitudinal direction A. The restricting mechanism 80 means a mechanism for restricting relative movement between the needle portion 11 and the movable portion 21 in the directions other than the longitudinal direction A.

A metal material suitable for plastic working is used as the material of the needle portion 11. Examples of the materials that can be used include a metallic material such as stainless steel, aluminum, aluminum alloy, titanium, titanium alloy, and magnesium alloy.

The holding portion 12 holds the proximal end portion of the needle portion 11. The holding portion 12 of the present embodiment includes a main body portion 51 and a locking claw portion 52. The main body portion 51 is provided with a holding opening 51a penetrating in the longitudinal direction A. The proximal end portion of the needle portion 11 is fixed to the main body portion 51 in a state of being inserted in the holding opening 51a. The locking claw portion 52 projects from the main body portion 51 toward the direction of removal A2. The locking claw portion 52 is positioned outside the needle portion 11 in the radial direction B of the needle portion 11. Also, the needle member 2 of the present embodiment is provided with a plurality of the locking claw portions 52 so as to surround the periphery of the needle portion 11 outside the needle portion 11 in the radial direction B. The locking claw portions 52 each include an extending portion 53 protruding from the main body portion 51 and an engagement projection 54 provided at an end portion of the extending portion 53 in the direction of removal A2. The extending portion 53 is resiliently deformable in a direction orthogonal to the longitudinal direction A with the position continuing to the main body portion 51 as a fulcrum. More specifically, the extending portion 53 of the present embodiment is resiliently deformable in the radial direction B of the needle portion 11 with the position continuing to the main body portion 51 as a fulcrum. The engagement projection 54 protrudes in the direction orthogonal to the longitudinal direction A from the end portion of the extending portion 53. An upper surface 54a located in the direction of removal A2 of each engagement projection 54 is inclined with respect to the longitudinal direction A so as to extend inward in the radial direction B as it proceeds the direction of insertion A1. The upper surfaces 54a of the engagement projections 54 are pressed outward in the radial direction B by being engaged with the main body portion 22, described below, of the movable member 3. A detailed description of this configuration will be given below.

Examples of the material of the holding portion 12 include a resin material. Examples of the resin material include: thermoplastic resins used in injection molding such as ABS resin, AS resin, polyethylene, polypropylene, polystyrene, polyvinyl chloride, polyvinylidene chloride resin, polyphenylene oxide, thermoplastic polyurethane, polymethylene methacrylate, polyoxyethylene, fluorine resin, polycarbonate, polyamide, acetal resin, acrylic resin, and polyethylene terephthalate; and thermosetting resins such as phenol resin, epoxy resin, silicone resin, and unsaturated polyester.

The movable member 3 includes the movable portion 21 and a main body portion 22.

The movable portion 21 is movable with respect to the needle portion 11 in the accommodation space 13 in the direction of insertion A1 of the needle portion 11. The movable portion 21 engages the clamping portion 31 of the needle portion 11 by moving in the direction of insertion A1 with respect to the needle portion 11. Accordingly, the movable portion 21 changes the form of the clamping portion 31 of the needle portion 1 from the first form to the second form. More specifically, the movable portion 21 of the present embodiment moves in the direction of insertion A1 with respect to the needle portion 11 to engage the projection portion 16 of the clamping portion 31 of the needle portion 11. Accordingly, the movable portion 21 of the present embodiment deforms the projection portion 16 and changes the form of the clamping portion 31 of the needle portion 11 from the first form to the second form. As described above, the first form of the clamping portion 31 means a form of clamping the sensor 100 accommodated in the accommodation space 13. Also, as described above, the second form of the clamping portion 31 means a form of not clamping the sensor 100 accommodated in the accommodation space 13.

As illustrated in FIG. 5A, FIG. 5B, FIG. 6A, and FIG. 6B, the movable portion 21 of the present embodiment includes a rod portion extending in the accommodation space 13 along the longitudinal direction A of the needle portion 11. The rod portion as the movable portion 21 of the present embodiment has a depressed cross-sectional shape. Therefore, a groove space 23 extending along the longitudinal direction A and capable of accommodating the sensor 100 is defined in the movable portion 21 of the present embodiment. In other words, the movable portion 21 of the present embodiment includes a groove-shaped rod portion. An opening portion 24 where the groove space 23 extending along the longitudinal direction A is connected to the outside is formed over the entire movable portion 21 in the longitudinal direction A.

The groove-shaped rod portion as the movable portion 21 of the present embodiment includes a first groove wall portion 21a and a second groove wall portion 21b arranged to oppose each other, and a groove bottom portion 21c continuing to respective end portions of the first groove wall portion 21a and the second groove wall portion 21b on one side. The first groove wall portion 21a, the second groove wall portion 21b, and the groove bottom portion 21c define the groove space 23. The opening portion 24 described above is formed at a position opposing the groove bottom portion 21c with the groove space 23 interposed therebetween.

The first groove wall portion 21a, the second groove wall portion 21b, and the groove bottom portion 21c of the present embodiment are each made of an elongated flat plate extending in the longitudinal direction A. That is, the groove-shaped rod portion as the movable portion 21 of the present embodiment forms a rectangular-shaped groove space 23 by three flat plate-shaped portions; the first groove wall portion 21a, the second groove wall portion 21b, and the groove bottom portion 21c. However, the cross-sectional profile orthogonal to the longitudinal direction A of the movable portion 21 is not limited to the shape of the rectangular-shaped groove as in the present embodiment. Rather, the movable portion 21 may be a movable portion having other cross-sectional profiles, such as a U-shape, C-shape, and the like.

In the groove-shaped rod portion as the movable portion 21 of the present embodiment, the first groove wall portion 21a extends longer in the direction of insertion A1 than the second groove wall portion 21b. In other words, the first groove wall portion 21a projects toward the direction of insertion A1 more than the second groove wall portion 21b. Also, although the groove bottom portion 21c of the present embodiment extends further in the direction of insertion A1 beyond the end portion of the first groove wall portion 21a in the direction of insertion A1, the position of the groove bottom portion 21c in the direction of insertion A1 is not specifically limited. Therefore, the position of the end portion of the groove bottom portion 21c in the direction of insertion A1 may be positioned in the direction of removal A2 than the first groove wall portion 21a. Also, the position of the end portion of the groove bottom portion 21c in the direction of insertion A1 may be positioned in the direction of removal A2 than the second groove wall portion 21b.

Although the opening portion 24 of the present embodiment is formed over the entirety of the movable portion 21 in a longitudinal direction A, it may be formed only part of the movable portion 21 in the longitudinal direction A. Conversely, the movable portion 21 may have a tubular portion partly in the longitudinal direction A. However, when the opening portion 24 is formed only partly in the longitudinal direction A, the opening portion 24 extends at least to the end surface of the movable portion 21 in the direction of insertion A1. In other words, the opening portion 24 is opened to the outside at least at the end surface of the movable portion 21 in the direction of insertion A1. The length of the opening portion 24 in the longitudinal direction A is not specifically limited. The length may be designed as needed according to the length of the sensor 100, described below, or the like.

Also, the sensor 100 of the present embodiment is connected to the controller 6 via a cable. Therefore, the movable portion 21 includes the opening portion 24 extending at least to the end surface in the direction of insertion A1. However, for example, in the case of the sensor or the like connected wirelessly with the controller 6, the opening portion 21 may have a tubular configuration having no opening portion 24 as a whole.

Further, as illustrated in FIG. 7, the movable portion 21 of the present embodiment is provided with a receiving groove 25 extending in the longitudinal direction A formed on an outer surface thereof. More specifically, the receiving groove 25 extending in the longitudinal direction A is formed on the outer surface of the groove bottom portion 21c of the movable portion 21. The movable portion 21 is disposed in the needle portion 11 with the rib 44 fitted to the receiving groove 25. With the receiving groove 25 and the rib 44, relative movement between the needle portion 11 and the movable portion 21 in the directions other than the longitudinal direction A may be restricted. In other words, in the present embodiment, the receiving groove 25 and the rib 44 constitute the restricting mechanism 80 configured to restrict the relative movement of the needle portion 11 and the movable portion 21 in directions other than the longitudinal direction A.

A metal material capable of plastic working is used as the material of the movable part 21. Examples of the materials that can be used include a metallic material such as stainless steel, aluminum, aluminum alloy, titanium, titanium alloy, and magnesium alloy.

The main body portion 22 holds the end portion of the movable portion 21 in the direction of removal A2. The main body portion 22 of the present embodiment is attached so as to be movable in the longitudinal direction A in the housing 4. The main body portion 22 of the present embodiment has an upper surface in the direction of removal A2 exposed from the housing 4 to the outside. Therefore, the operator of the insertion device 1 can move the main body portion 22 in the direction of insertion A1 by pressing the main body portion 22 exposed from the housing 4 in the direction of insertion A1. Accordingly, the movable portion 21 attached to the main body portion 22 can also move in the accommodation space 13 of the needle portion 11 in the direction of insertion A1. In other words, the main body portion 22 also serves as an operation unit of the insertion device 1.

The main body portion 22 includes an engagement portion 61 configured to press the locking claw portions 52 of the holding portion 12 of the needle member 2 outward in the radial direction B of the needle portion 11. The main body portion 22 defines an engagement depression 62, in which the engagement projection 54 of the locking claw portion 52 can fit, at a position adjacent to the engagement portion 61 in the direction of removal A2. The engagement depression 62 is depressed inward with respect to the engagement portion 61 in the radial direction B. As illustrated in FIG. 1 to FIG. 4, the engagement portion 61 may be formed, for example, of a disk portion. Also, as illustrated in FIG. 1 to FIG. 4, the engagement depression 62 is formed by an annular groove located adjacent to the disk portion as the engagement portion 61 in the direction of removal A2 and depressed inward with respect to an outer edge of the disk portion in the radial direction B. However, the configurations of the engagement portion 61 and the engagement depression 62 are not limited to the shape and the position illustrated in the present embodiment.

As illustrated in FIG. 1 to FIG. 3, the insertion device 1 of the present embodiment can insert the needle portion 11 and the sensor 100 into the living body by pushing the main body portion 22 in the direction of insertion A1. At that time, the engagement portion 61 of the main body portion 22 engages the upper surfaces 54a located in the direction of removal A2 of the engagement projections 54 of the locking claw portions 52 and presses the engagement projections 54 outward in the radial direction B. Accordingly, as illustrated in FIG. 2, the extending portions 53 of the locking claw portions 52 resiliently deform outward in the radial direction B. In other words, the plurality of locking claw portions 52 located in the outside periphery of the needle portion 11 in the radial direction B resiliently deform outward in the radial direction B away from each other. Therefore, as illustrated in FIG. 3, the engagement portion 61 of the main body portion 22 can pass over the engagement projections 54 in the direction of insertion A1 while sliding on the upper surfaces 54a of the engagement projections 54.

As illustrated in FIG. 3, when the engagement portion 61 of the main body portion 22 passes over the engagement projections 54 of the needle member 2, the engagement projections 54 fit the engagement depression 62 of the main body portion 22. Accordingly, the main body portion 22 of the movable member 3 and the holding portion 12 of the needle member 2 interfere in the longitudinal direction A. In other words, the needle member 2 and the movable member 3 are integrally movable in the longitudinal direction A. Specifically, when the movable member 3 is moved in the direction of removal A2, the inner surface of the engagement depression 62 of the main body portion 22 of the movable member 3 in the direction of insertion A1 comes into attachment with the outer surfaces of the engagement projection 54 of the holding portion 12 of the needle member 2 in the direction of insertion A1. Accordingly, the needle member 2 and the movable member 3 can be united and moved together in the direction of removal A2. Therefore, as illustrated in FIG. 4, when removing the needle portion 11 from the living body, the movable portion 21 in the needle portion 11 can be removed from the living body together with the needle portion 11.

Examples of the material of the main body portion 22 include a resin material. Examples of the resin material include: thermoplastic resins used in injection molding such as ABS resin, AS resin, polyethylene, polypropylene, polystyrene, polyvinyl chloride, polyvinylidene chloride resin, polyphenylene oxide, thermoplastic polyurethane, polymethylene methacrylate, polyoxyethylene, fluorine resin, polycarbonate, polyamide, acetal resin, acrylic resin, and polyethylene terephthalate; and thermosetting resins such as phenol resin, epoxy resin, silicone resin, and unsaturated polyester.

The housing 4 is an exterior member configured to cover the needle member 2, the movable member 3, the biasing member 5, the controller 6, and the sensor 100, which is described below. As illustrated in FIG. 1 to FIG. 4, the housing 4 of the present embodiment includes a cylindrical member 71 configured to cover the periphery of the needle member 2, the movable member 3, the biasing member 5, the controller 6, and the sensor 100, described below, in the radial direction B, and a base plate 72 configured to cover an end surface of the cylindrical member 71 in the direction of insertion A1 in a state in which the needle portion 11 is in the waiting position (see FIG. 1). The base plate 72 is attachable to and detachable from the cylindrical member 71.

A surface of the base plate 72 on the side of the direction of insertion A1 constitutes an attachment surface 72a that is brought into attachment with the living body surface BS when the needle portion 11 and the sensor 100 are inserted into the living body. The base plate 72 includes a through-hole 74 that penetrates in the longitudinal direction A. When the needle portion 11 in the waiting position (see FIG. 1) moves to the insertion position (see FIG. 3), the needle portion 11 protrudes from the attachment surface 72a in the direction of insertion A1 through the through-hole 74.

The configuration of the housing 4 is not specifically limited. In the present embodiment, the needle member 2 and the movable member 3 are movably attached to the housing 4 in the longitudinal direction A but may be movably attached to a member other than the housing 4.

Although the insertion device 1 of the present embodiment includes the housing 4, a configuration without the housing 4 is also applicable. However, like the housing 4 of the present embodiment, the insertion device 1 preferably includes a member that covers at least the outside periphery of the needle portion 11 in the waiting position in the radial direction B for reducing the probability that the health care workers or the patients erroneously touch the needle member 2.

Also, although the housing 4 of the present embodiment is configured such that the cylindrical member 71 and the base plate 72 are attachable and detachable, it is not limited thereto, and both members may be formed integrally to each other. However, by configuring both members attachable and detachable, the size of a portion to be implanted on the living body surface BS can easily be reduced so that the burden of the subject can be alleviated.

Examples of the material of the housing 4 include a resin material. Examples of the resin material include: thermoplastic resins used in injection molding such as ABS resin, AS resin, polyethylene, polypropylene, polystyrene, polyvinyl chloride, polyvinylidene chloride resin, polyphenylene oxide, thermoplastic polyurethane, polymethylene methacrylate, polyoxyethylene, fluorine resin, polycarbonate, polyamide, acetal resin, acrylic resin, and polyethylene terephthalate; and thermosetting resins such as phenol resin, epoxy resin, silicone resin, and unsaturated polyester.

The biasing member 5 of the present embodiment is resiliently deformable in the longitudinal direction A. The biasing member 5 of the present embodiment is a coil spring which resiliently deforms in the longitudinal direction A. The coil spring as the biasing member 5 is disposed between the holding portion 12 of the needle member 2 and the base plate 72 of the housing 4. Therefore, the coil spring as the biasing member 5 of the present embodiment is subject to compression deformation by the needle portion 11 moving from the waiting position (see FIG. 1) to the insertion position (see FIG. 3). Also, by releasing a restoring force of the coil spring as the biasing member 5 in a state in which the needle portion 11 is in the insertion position (see FIG. 3), the needle portion 11 can be moved from the insertion position (see FIG. 3) in the direction of removal A2.

Therefore, in the insertion device 1 of the present embodiment, when the needle member 11 and the sensor 100 are inserted into the living body, the needle member 2 and the movable member 3 described above are moved in the direction of insertion A1 against the restoring force of the coil spring as the biasing member 5. Accordingly, as illustrated in FIG. 2 and FIG. 3, the needle member 2 and the movable member 3 moves in the direction of insertion A1 and the needle portion 11 and the sensor 100 are inserted into the living body. By releasing the pressing force in the direction of insertion A1 applied to the needle member 2 and the movable member 3 after the insertion of the needle portion 11 and the sensor 100 into the living body, the needle member 2 and the movable member 3 move in the direction of removal A2 by the restoring force of the coil spring as the biasing member 5. Accordingly, the needle portion 11 can be removed from the living body with the sensor 100 left in the living body. In the present embodiment, by the restoring force of the coil spring as the biasing member 5, the needle portion 11 returns from the insertion position (see FIG. 3) to a position (the waiting position as in the FIG. 1, for example) of being accommodated in the housing 4 again (see FIG. 4).

As described above, although the biasing member 5 of the present embodiment is composed of the coil spring, it is not limited to the coil spring, and other resilient members may be used, for example. Also, the insertion device 1 may be configured not to include the biasing member 5.

The controller 6 is connected to the sensor 100 electrically or optically. Therefore, the controller 6 can receive detected information from the sensor 100 implanted in the living body. Also, as described above, the controller 6 analyzes the detection signal received from the sensor 100 and transmits the result of analysis to an external device such as a display apparatus as needed. The controller 6 includes a processor, a memory, and a battery.

As illustrated in FIG. 1 to FIG. 4, the controller 6 of the present embodiment moves together with the needle portion 11 and the sensor 100 in the direction of insertion A1 when the needle portion 11 and the sensor 100 are inserted into the living body. More specifically, the controller 6 of the present embodiment is held by the needle member 2 in a state in which the needle portion 11 is in the waiting position (see FIG. 1). When the needle portion 11 moves from the waiting position (see FIG. 1) to the insertion position (see FIG. 3), the controller 6 moves together with the needle member 2 in the direction of insertion A1. When the needle portion 11 reaches the insertion position (see FIG. 3), the controller 6 engages the base plate 72 of the housing 4, and the state of being held by the needle member 2 is released. Accordingly, the controller 6 assumes a state of being held on the base plate 72. Therefore, when the needle portion 11 is removed from the living body, that is, when the needle portion 11 returns from the insertion position to the waiting position, the needle member 2 moves in the direction of removal A2. However, the controller 6 does not move in the direction of removal A2 and remains on the base plate 72 of the housing 4.

The sensor 100 of the present embodiment is a linear member to be accommodated in the accommodation space 13 of the needle portion 11. As the sensor 100, a member configured to detect an electric signal corresponding to an amount or concentration of the substance to be measured can be used. The sensor 100 extends in the accommodation space 13 along the longitudinal direction A of the needle portion 11.

The sensor 100 may be, for example, a wire electrode having a circular cross-section. The wire electrode is accommodated in the accommodation space 13 of the needle portion 11. The outer diameter of the wire electrode may be, for example, from 0.02 mm to 0.2 mm. For example, two wire electrodes; a working electrode and a reference electrode, may be accommodated in the accommodation space 13. The working electrode is formed basically of a core having a conductive surface and may be configured to include a detection portion 101 provided on an outer wall of the core and configured to detect the substance to be measured, and a protecting portion made of an insulating material coated on the outer wall of the core. Changes in electrical characteristics of the substance to be measured can be detected by the detection portion 101. The detection portion 101 is formed on a core surface by using thin-film forming means such as dipping, electropolymerization, sputtering, and the like. A reagent that reacts specifically with the substance to be measured is applied on a surface of the working electrode. When the substance to be measured is glucose, a reagent containing glucose oxidase or a phenylboronic acid compounds is used. The reference electrode is used as a reference electrode for the working electrode described above. A single wire electrode formed by winding the reference electrode or a counter electrode in a coil shape around the working electrode is also applicable. Alternatively, three wire electrodes may be disposed in the accommodation space 13. The three wire electrodes may be used to constitute the working electrode, the reference electrode, and the counter electrode. Alternatively, the needle portion 11 itself may be used as the reference electrode or the counter electrode. Information on the substance to be measured detected by the detection portion 101 of the working electrode is transmitted to the controller 6.

Next, the details of the operation of the needle portion 11, the movable portion 21, and the sensor 100 when inserting and implanting the sensor 100 into the living body by using the insertion device 1 will be described. FIG. 8A is a drawing illustrating the needle portion 11, the movable portion 21, and the sensor 100 in the state in which the needle portion 11 is in the waiting position (see FIG. 1). FIG. 8B is a drawing illustrating the needle portion 11, the movable portion 21, and the sensor 100 in the state in which the needle portion 11 is in the course of moving from the waiting position (see FIG. 1) to the insertion position (see FIG. 3). FIG. 8C is a drawing illustrating the needle portion 11, the movable portion 21, and the sensor 100 in the state in which the needle portion 11 is in the insertion position (see FIG. 3). FIG. 8D is a drawing illustrating the needle portion 11, the movable portion 21, and the sensor 100 in the state in which the needle portion 11 is in the course of returning into the housing 4 after the sensor 100 has been implanted in the insertion position (see FIG. 3).

As illustrated in FIG. 8A, in a state in which the needle portion 11 is in the waiting position, the sensor 100 is clamped by the clamping portion 31 of the needle portion 11. Specifically, the sensor 100 is clamped between the inner surface of the sidewall portion 15 and the projection portion 16, which constitute the clamping portion 31. In other words, the clamping portion 31 illustrated in FIG. 8A is in the first form for clamping the sensor 100 in the accommodation space 13. More specifically, the sensor 100 is clamped between the inner surface of the second side plate portion 15b of the sidewall portion 15 and the flap distal end portion 43 of the flap 41 as the projection portion 16 at a position in the direction of removal A2 with respect to the detection portion 101. In this state, the end portion of the movable portion 21 in the direction of insertion A1 is located in the direction of removal A2 with respect to the clamping portion 31.

Although the clamping portion 31 of the present embodiment clamps the sensor 100 at a predetermined position located in the direction of removal A2 with respect to the detection portion 101, the position is not specifically limited as long as it is a position other than the detection portion 101. However, in order to reliably insert the detection portion 101 to the desired depth in the living body, the clamping portion 31 preferably clamps the distal end portion of the sensor 100 in the direction of insertion A1. Further, as in the present embodiment, the clamping portion 31 preferably clamps the sensor 100 at a predetermined position located in the direction of removal A2 with respect to the detection portion 101. In this configuration, the movable portion 21 moving in the direction of insertion A1 and engaging the clamping portion 31 is restrained from sliding together with the detection portion 101, whereby damage of the detection portion 101 may be reduced.

As illustrated in FIG. 1 to FIG. 3, the needle member 2 and the movable member 3 both move in the direction of insertion A1 in the course of movement of the needle portion 11 from the waiting position (see FIG. 1) to the insertion position (see FIG. 3). As illustrated in FIG. 1 to FIG. 3, the relative positional relationship between the needle member 2 and the movable member 3 in the longitudinal direction A varies in the course of movement of the needle portion 11 from the waiting position (see FIG. 1) to the insertion position (see FIG. 3). In other words, the needle member 2 and the movable member 3 both move in the direction of insertion A1 in the course of movement of the needle portion 11 from the waiting position (see FIG. 1) to the insertion position (see FIG. 3), and the movable member 3 moves also relatively to get closer to the needle member 2 in the direction of insertion A1. Therefore, as illustrated in FIG. 8B, the movable portion 21 of the movable member 3 moves in the direction of insertion A1 with respect to the needle portion 11 of the needle member 2 in the course of movement of the needle portion 11 from the waiting position (see FIG. 1) to the insertion position (see FIG. 3). Accordingly, the movable portion 21 moves to a position engaging the clamping portion 31 of the needle portion 11. FIG. 8B illustrates a state in which the end portion of the first groove wall portion 21a of the movable portion 21 in the direction of insertion A1 engages the flap 41 as the projection portion 16, which constitutes the clamping portion 31 of the needle portion 11.

As illustrated in FIG. 8C, the end portion of the first groove wall portion 21a of the movable portion 21 in the direction of insertion A1 engages the inclined portion 42 of the flap 41 to resiliently deform the inclined portion 42 so as to get closer to the first side plate portion 15a. Therefore, as illustrated in FIG. 8C, the flap distal end portion 43 of the flap 41 moves away from the second side plate portion 15b. Accordingly, the clamped state of the sensor 100 by the clamping portion 31 of the needle portion 11 may be released. In this manner, when the needle portion 11 reaches the insertion position (see FIG. 3 and FIG. 8C), the sensor 100 is released from being clamped by the clamping portion 31 of the needle portion 11, and a state of being movable relative to the needle portion 11 in the longitudinal direction A is achieved. In other words, the clamping portion 31 illustrated in FIG. 8C is in the second form for not clamping the sensor 100 in the accommodation space 13.

In this manner, the movable portion 21 of the present embodiment changes the form of the clamping portion 31 from the first form to the second form by moving in the direction of insertion A1 with respect to the needle portion 11 and engaging the projection portion 16 and deforming the projection portion 16. Accordingly, the sensor 100 is unlikely to be caught by the needle portion 11 when the needle portion 11 is removed from the living body. Therefore, as illustrated in FIG. 8D, the needle portion 11 and the movable portion 21 can easily be removed from the living body with the sensor 100 left at a predetermined depth in the living body.

As described above, in the insertion device 1 of the present embodiment, the needle portion 11 clamps the sensor 100 while the needle portion 11 moves from the waiting position (see FIG. 1 and FIG. 8A) to the insertion position (see FIG. 3 and FIG. 8C). Therefore, the sensor 100 can easily be inserted to the desired depth in the living body. When the needle portion 11 reaches the insertion position, the clamped state of the sensor 100 by the needle portion 11 is released. Therefore, the sensor 100 is unlikely to be caught by the needle portion 11 when the needle portion 11 is removed from the living body. Therefore, the sensor 100 is restrained from moving in the direction of removal A2 and being displaced from the desired depth when the needle portion 11 is removed from the living body. Therefore, the sensor 100 can easily be implanted at the desired depth in the living body.

The insertion device 1 of the present embodiment includes the restricting mechanism 80. Specifically, the insertion device 1 of the present embodiment includes the rib 44 of the needle portion 11 and the receiving groove 25 of the movable portion 21. Therefore, the needle portion 11 and the movable portion 21 can easily be moved in the longitudinal direction A. The first groove wall portion 21a and the second groove wall portion 21b of the movable portion 21 of the present embodiment are interposed between the first side plate portion 15a and the second side plate portion 15b, opposing each other, of the needle portion 11. Therefore, the movable portion 21 is restricted from moving in an opposing direction between the first side plate portion 15a and the second side plate portion 15b of the needle portion 11. Therefore, in the insertion device 1 of the present embodiment, in addition to the rib 44 and the receiving groove 25 described above, the first groove wall portion 21a and the second groove wall portion 21b of the movable portion 21, as well as the first side plate portion 15a and the second side plate portion 15b of the needle portion 11, constitute the restricting mechanism 80.

FIG. 9 is a drawing illustrating a needle portion 111 as a modification of the needle portion 11. FIG. 9 is a cross-sectional view of the needle portion 111 and the movable portion 21 taken along a cross section orthogonal to the longitudinal direction A. As illustrated in FIG. 9, the needle portion 111 is provided with a first turned-back portion 15d continuing to the other end of the first side plate portion 15a, which is the opposite side of the one end continuing to the third side plate portion 15c. Also, the needle portion 111 is provided with a second turned-back portion 15e continuing to the other end of the second side plate portion 15b, which is the opposite side of the one end continuing to the third side plate portion 15c. The one end of the first groove wall portion 21a of the movable portion 21 on the opposite side from the one end continuing to the groove bottom portion 21c is covered with the first turned-back portion 15d. Also, the end of the second groove wall portion 21b of the movable portion 21 on the opposite side from the one end continuing to the groove bottom portion 21c is covered with the second turned-back portion 15e. To allow the needle portion 111 and the movable portion 21 to slide in the longitudinal direction A, a clearance of 0.01 mm to 0.02 mm may be provided between the first turned-back portion 15d and the first groove wall portion 21a and between the second turned-back portion 15e and the second groove wall portion 21b. By providing the first turned-back portion 15d and the second turned-back portion 15e in this configuration, the movable portion 21 is restrained from slipping off a gap 114 of the needle portion 111. That is, in the example illustrated in FIG. 9, the first turned-back portion 15d and the second turned-back portion 15e also constitute the restricting mechanism 80 configured to restrict the relative movement of the needle portion 111 and the movable portion 21 in directions other than in the longitudinal direction A. Also, in the needle portion 111 and the movable portion 21 in FIG. 9, the receiving groove 25 and the rib 44 may not be provided.

In this manner, the configuration of the restricting mechanism 80 is not specifically limited as long as it is configured to restrict the relative movement of the needle portion and the movable portion in directions other than the longitudinal direction A.

Referring next to FIG. 10 and FIG. 11, a method of manufacturing the needle portion 11 described above will be described. FIG. 10 is a flowchart showing an example of the method of manufacturing the needle portion 11. FIG. 11 is a drawing illustrating an overview of respective processes of the method of manufacturing illustrated in FIG. 10. The method of manufacturing the needle portion 11 illustrated in FIG. 10 includes: a punching process S1 for punching out a rectangular plate-shaped unfolded body 120 that becomes the needle portion 11, a press process S2 for pressing the unfolded body 120 by a pressing and shaping machine 500 to form a rod member 121 having a rectangular groove-shaped cross-section; a flap push-in process S3 for pushing a rectangular strip that becomes the flap 41, to form the flap 41, and a sharpening process S4 for forming a cutting edge on one end portion of the rod member 121 having a rectangular groove-shaped cross-section. In the method of manufacturing the needle portion 11 illustrated in FIG. 10, in the punching process S1 for forming the rectangular plate-shaped unfolded body 120, a slit 501 for forming a rectangular strip that becomes the flap 41, is formed. Therefore, in the flap push-in process S3, the flap 41 is formed by pushing the rectangular strip formed by being surrounded by the slit 501. In the press process S2, the rib 44, which constitutes the restricting mechanism 80 of the needle portion 11, is preferably formed at the same time. Also, in the press process S2, the rod member 121 having a rectangular groove-shaped cross-section is formed by gradually curving by using a plurality of molds in sequence. In the method of manufacturing the needle portion 11 illustrated in FIG. 10, the sharpening process S4 is included after the formation of the rod member 121 having the rectangular groove-shaped cross-section. However, a cutting edge shape may be formed in advance at a distal end portion of the unfolded body 120 in the punching process S1.

In addition, the method of manufacturing the needle portion 11 illustrated in FIG. 10 may further include other processes such as a grinding process of the needle portion 11 in addition to the processes S1 to S4 described above. In addition, a process of forming the first turned-back portion 15d and the second turned-back portion 15e illustrated in FIG. 9 may further be included.

The needle member 2 is manufactured by joining the needle portion 11 manufactured by the method of manufacturing illustrated in FIG. 10 to the holding portion 12. The needle portion 11 and the holding portion 12 are joined, for example, by fusion bonding, adhesion, and the like.

FIG. 12 is a flowchart illustrating a modified example of a method of manufacturing the needle portion 11 illustrated in FIG. 10. The needle portion 11 is formed from the flat plate-shaped unfolded body 120 in the method of manufacturing illustrated in FIG. 10. However, in the method of manufacturing illustrated in FIG. 12, the needle portion 11 is formed from the half-tubular member. Specifically, the method of manufacturing the needle portion 11 illustrated in FIG. 12 includes: a half-tube acquiring process S1 for acquiring the half-tubular member; a flap cutting process S2 for forming a rectangular strip that becomes the flap 41, by cutting part of the half-tubular member; a rib forming process S3 for forming the rib 44 on a depressed-shaped inner surface of the half-tubular member; a press process S4 for pressing the half-tubular member by the pressing and shaping machine 500 to form a rod member 121 having a rectangular groove-shaped cross-section; a flap push-in process S5 for pushing the rectangular strip that becomes the flap 41, to form the flap 41; and a sharpening process S6 for forming a cutting edge on one end portion of the rod member 121 having a rectangular groove-shaped cross-section.

In the flap cutting process S2, a slit 501 is formed by, for example, laser processing. In the flap push-in process S5, the flap 41 is formed by pushing the rectangular strip formed by being surrounded by the slit 501. In FIG. 12, although the rib forming process S3 is included separately from the press process S4, the rib 44 may be formed at the same time in the press process S4. In the method of manufacturing the needle portion 11 illustrated in FIG. 12, the sharpening process S6 is included after the formation of the rod member 121 having the rectangular groove-shaped cross-section. However, the cutting edge shape may be formed in advance before the press process S4.

The insertion device and the needle member according to the present disclosure is not limited to the specific configuration and process described in the embodiments above, and various modifications and changes can be made without departing from the scope of the appended claims.

REFERENCE CHARACTER LIST

1: insertion device
2: needle member
3: movable member
4: housing
5: biasing member
6. controller
11, 111: needle portion
12: holding portion
13: accommodation space
14, 114: gap
15: sidewall portion
15a: first side plate portion
15b: second side plate portion
15c: third side plate portion
15d: first turned-back portion
15e: second turned-back portion
16: projection portion
21: movable portion
21a: first groove wall portion
21b: second groove wall portion
21c: groove bottom portion
22: main body portion
23: groove space
24: opening portion
25: receiving groove
31: clamping portion
41: flap
41a: first outer edge portion
41b: second outer edge portion
41c: third outer edge portion
42: inclined portion
43: flap distal end portion
44: rib
51: main body portion
51a: holding opening
52: locking claw portion 53: extending portion
54: engagement projection
54a: upper surface of engagement projection
61: engagement portion
62: engagement depression
71: cylindrical member
72: base plate
72a: attachment surface
74: through-hole
80: restricting mechanism
100: sensor (medical device)
101: detection portion
120: unfolded body
121: rod member
500: pressing and shaping machine
501: slit
A: longitudinal direction of needle portion
A1: direction of insertion
A2: direction of removal
B: radial direction of needle portion
BS: living body surface

The invention claimed is:

1. An insertion device for inserting a medical device into a living body, comprising:
   a needle portion comprising:
      a sidewall internally defining an accommodation space configured to accommodate the medical device, and
      a flap comprising a portion of the sidewall that is bent inward so as to project into the accommodation space, wherein:
      the needle portion is configured to be inserted into the living body together with the medical device accommodated in the accommodation space; and
   a movable portion that is movable with respect to the needle portion in the accommodation space in a direction of insertion of the needle portion, wherein:
   the movable portion is configured to move in the direction of insertion with respect to the needle portion and contact the flap so as to move the flap from (i) a first position in which the flap clamps the medical device against the sidewall to (ii) a second position in which the flap does not clamp the medical device against the sidewall.

2. The insertion device according to claim 1, wherein the movable portion defines a groove space extending along the direction of insertion that is located within the accommodation space and configured to accommodate the medical device.

3. The insertion device according to claim 2, comprising a restricting mechanism configured to restrict relative movement of the needle portion and the movable portion in directions other than a longitudinal direction of the needle portion.

4. The insertion device according to claim 1, comprising a restricting mechanism configured to restrict relative movement of the needle portion and the movable portion in directions other than a longitudinal direction of the needle portion.

5. The insertion device according to claim 1, wherein:
the flap comprises an inclined portion that extends from the sidewall in the direction of insertion, and
the movable portion is configured to move in the direction of insertion with respect to the needle portion and contact the inclined portion so as to move the flap from (i) the first position in the which the flap clamps the medical device against the sidewall to (ii) the second position in which the flap does not clamp the medical device against the sidewall.

6. The insertion device according to claim 5, wherein:
the flap further comprises a distal end portion that has an angle of inclination, with respect to a longitudinal direction of the needle portion, smaller than that of the inclined portion, and
in the first position, the distal end portion clamps the medical device against the sidewall.

7. A needle member comprising:
   a needle portion comprising:
      a sidewall internally defining an accommodation space configured to accommodate a medical device, and
      a flap comprising a portion of the sidewall that is bent inward so as to project into the accommodation space, wherein:
      the needle portion is configured to be inserted into a living body together with the medical device accommodated in the accommodation space; and
   the flap is configured to be contacted so as to move from (i) a first position in which the flap clamps the medical device against the sidewall to (ii) a second position in which the flap does not clamp the medical device against the sidewall.

8. A method for inserting a medical device into a living body, the method comprising:
   providing an insertion device comprising:
      a needle portion comprising:
         a sidewall internally defining an accommodation space configured to accommodate the medical device, and
         a flap comprising a portion of the sidewall that is bent inward so as to project into the accommodation space, wherein:
         the needle portion is configured to be inserted into the living body together with the medical device accommodated in the accommodation space; and
      a movable portion that is movable with respect to the needle portion in the accommodation space in a direction of insertion of the needle portion; and
   inserting, into the living body, the needle portion together with the medical device accommodated in the accommodation space, which causes the movable portion to move in the direction of insertion with respect to the needle portion and contact the flap so as to move the flap from (i) a first position in which the flap clamps the medical device against the sidewall to (ii) a second position in which the flap does not clamp the medical device against the sidewall.

* * * * *